US008030318B2

(12) United States Patent
Simmen et al.

(10) Patent No.: US 8,030,318 B2
(45) Date of Patent: Oct. 4, 2011

(54) FUSED BICYCLIC INHIBITORS OF HCV

(75) Inventors: Kenneth Alan Simmen, Tervuren (BE); Dominique Louis Nestor Ghislain Surleraux, Braine-le-château (BE); Tse-I Lin, Mechelen (BE); Oliver Lenz, Sint-Katelijne-Waver (BE); Pierre Jean-Marie Bernard Raboisson, Sterrebeek (BE); Sarvajit Chakravarty, Mountain View, CA (US); Barry Patrick Hart, Palo Alto, CA (US)

(73) Assignee: Tibotec Pharmaceuticals Ltd., Co Cork (IE)

( * ) Notice: Subject to any disclaimer, the term of this patent is extended or adjusted under 35 U.S.C. 154(b) by 2 days.

(21) Appl. No.: 11/909,118

(22) PCT Filed: Mar. 27, 2006

(86) PCT No.: PCT/EP2006/061070
§ 371 (c)(1),
(2), (4) Date: Sep. 19, 2007

(87) PCT Pub. No.: WO2006/100310
PCT Pub. Date: Sep. 28, 2006

(65) Prior Publication Data
US 2008/0182863 A1    Jul. 31, 2008

Related U.S. Application Data

(60) Provisional application No. 60/665,151, filed on Mar. 25, 2005, provisional application No. 60/680,405, filed on May 12, 2005.

(51) Int. Cl.
*A61K 31/519* (2006.01)
*C07D 471/04* (2006.01)

(52) U.S. Cl. .................................. 514/264.11; 544/279

(58) Field of Classification Search ............. 514/264.11; 544/279
See application file for complete search history.

(56) References Cited

U.S. PATENT DOCUMENTS

| | | | |
|---|---|---|---|
| 3,873,545 | A | 3/1975 | Osselaere et al. |
| 6,476,031 | B1 | 11/2002 | Chakravarty et al. |
| 2004/0032430 | A1 | 2/2004 | Yung et al. |
| 2004/0038856 | A1 | 2/2004 | Chakravarty et al. |
| 2004/0132159 | A1 | 7/2004 | Zhong et al. |
| 2005/0004143 | A1 | 1/2005 | Dugar et al. |
| 2007/0155716 | A1 | 7/2007 | Simmen et al. |
| 2009/0131460 | A1 | 5/2009 | Simmen et al. |
| 2009/0156595 | A1 | 6/2009 | Raboisson et al. |

FOREIGN PATENT DOCUMENTS

| | | |
|---|---|---|
| GB | 2 295 387 A | 5/1996 |
| JP | 2003/321472 | 11/2003 |
| WO | WO-95/19774 | 7/1995 |
| WO | WO-00/12497 | 3/2000 |
| WO | WO-01/047921 A1 | 7/2001 |
| WO | WO-02/22601 A1 | 3/2002 |
| WO | WO-02/076976 A2 | 10/2002 |
| WO | WO-03/059913 A1 | 7/2003 |
| WO | WO-03/077921 A1 | 9/2003 |
| WO | WO-03/078423 A1 | 9/2003 |
| WO | WO-03/078426 A1 | 9/2003 |
| WO | WO-03/078427 A1 | 9/2003 |
| WO | WO 03/097615 A | 11/2003 |
| WO | WO-2004/020584 A2 | 3/2004 |
| WO | WO-2004/024159 A1 | 3/2004 |
| WO | WO 2004/047818 A | 6/2004 |
| WO | WO-2004/048930 A2 | 6/2004 |
| WO | WO-2004/065392 A1 | 8/2004 |
| WO | WO-2004/074270 A2 | 9/2004 |
| WO | WO-2004/087056 A2 | 10/2004 |
| WO | WO 2005/032481 A | 4/2005 |
| WO | WO 2006/100310 A1 | 9/2006 |
| WO | WO-2006/105063 A1 | 10/2006 |

OTHER PUBLICATIONS

Murata et al. (Virology, vol. 331, pp. 407-417; 2005).*
Stella (Expert Opinion on Therapeutic Patents, Prodrugs as therapeutics, col. 14, No. 3, pp. 277-280; 2004).*
Wolff (Burger's Medicinal Chemistry, 5th Ed., vol. 1, pp. 975-977; 1994).*
Testa (Biochemical Pharmacology, Prodrug Research: futile or fertile?, vol. 68, pp. 2097-2106; 2004).*
Ettmayer et al. (Medicinal Chemistry, Lessons Learned from Marketed and Investigational Prodrugs, vol. 47, No. 10, pp. 2394-2404; 2004).*
Cheng et al. (Oncogene, vol. 23, pp. 7821-7838; 2004).*
N. Dumont, et al., Transforming Growth Factor-β and Breast Cancer Tumor Promoting Effects of Transforming Growth Factor-β, *Breast Cancer Research*, 2(2):125-132, 2000.
M. de Caestecker, et al., Role of Transforming Growth Factor-β Signaling in Cancer, *Journal of the National Cancer Institute*, 92(17):I388-1402, 2000.
J. Munger, et al., The Integrin αvβ6 Binds and Activates Latent TGFβ1 : A Mechanism for Regulating Pulmonary Inflammation and Fibrosis, *Cell*, 96:319-328, 1999.
S. Crawford, et al., Thrombospondin-1 Is a Major Activator of TGF-β1 In Vivo; *Cell* 93:1159-1170, 1998.
R. Lyons, et al., Transforming Growth Factors and the Regulation of Cell Proliferation, *Eur. J. Biochem*, 187:467-473, 1990. T. Kimura, et al., Association of Transforming Growth Factor-β1 Functional Polymorphisms with Natural Clearance of Hepatitis C Virus, *Brief Report*, 193:1371-1374, 2006.
G. Breipohl, et al., Novel Synthetic Routes to PNA Monomers and PNA-DNA Linker Molecules, *Tetrahedron*, 53(43):14671-14686, 1997.
Q. Choo, et al., Isolation of a cDNA Clone Derived from a Blood-Borne Non-A, Non-B Viral Hepatitis Genome, *Science*, 244:359-362, 1989.
C. Cywin, et al., Discovery and SAR of Novel [1,6]Naphthyridines as Potent Inhibitors of Spleen Tyrosine Kinase (SYK), *Bioorganic & Medicinal Chemistry Letters*, 13:1415-1418, 2003.

(Continued)

*Primary Examiner* — Phyllis G Spivack
*Assistant Examiner* — Nelson C Blakely, III
(74) *Attorney, Agent, or Firm* — Rajiv Shah, Esquire; Johnson & Johnson

(57) ABSTRACT

Substituted fused bicyclic pyrimidine compounds having an amide-substituted pyridylamine group at C-4 of the pyrimidine ring are useful in the treatment of conditions associated with HCV.

3 Claims, No Drawings

OTHER PUBLICATIONS

D. Harrison, et al., The Synthesis of Some Cyclic Hydroxamic Acids from o-Aminocarboxylic Acids, *Journal of the Chemical Society Abstracts*, XP002373945, Database accession No. 1960: 118360, 2157-2160, 1960.

W. Kim, The Burden of Hepatitis C in the United States, *Hepatology*, 36(5): Suppl. 1:S30-S34, 2002.

A. Kolykhalov, et al., Hepatitis C Virus-Encoded Enzymatic Activities and Conserved RNA Elements in the 3' Nontranslated Region Are Essential for Virus Replication In Vivo, *Journal of Virology*, 74(4):2046-2051, 2000.

N. Krieger, et al., Enhancement of Hepatitis C Virus RNA Replication by Cell Culture-Adaptive Mutations, *Journal of Virology*, 75(10):4614-4624, 2001.

G. Lauer, et al., Hepatitis C Virus Infection, *N. Engl J Med*, 345(I):41-52, 2001.

V. Lohmann, et al., Replications of Subgenomic Hepatitis C Virus RNAs in a Hepatoma Cell Line, *Science*, 285:110-113, 1999.

S. Nishikawa, et al., Cytokinin Activity of 4-Aminopyridopyrimidines Towards the Growth of Tobacco Callus, *Biosci. Biotech. Biochem.*, 58(9):1709-1710, 1994.

H. Wamhoff, Dihalogentriphenylphosphorane in der heterocyclensynthese, 29. Eine einfache Synthese von Pteridin-4-onen aus 3-Amino-2-pyrazincarbonsäuremethylester and Pyrazino[3,1]oxazin-4-onen, Synthesis, 405-410, 1994. (English Language Abstract).

B. Vereček, et al., Neighboring Group Interaction in Ortho-Substituted Heterocycles.2. 1,2,4- Oxadiazolylpyridines and Pyrido[2,3-d]pyrimidine 3-Oxides, *J. Org. Chem.*, 44(10):1695-1699, 1979.

National Institutes of Health Consensus Development Conference Statement: Management of Hepatitis C: 2002-Jun. 10-12, 2002, *Hepatology*, S3-S20, 2002.

T. Sekiguchi, et al., Reduction of Virus Burden-Induced Splenectomy in Patients With Liver Cirrhosis Related to Hepatitis C Virus Infection, *World J. Gastroenterol*, 12(13):2089-2094, 2006.

M. De Mitri, et al., HCV-Associated Liver Cancer Without Cirrhosis, *Lancet*, Abstract: 345(8947), 1995.

M. Nogradi, Dimethyl-β-Cyclodextrin, *Drugs of the Future*, 9(8):577-578, 1984.

K. Cooper, et al., Bicyclo[3.3.0]octenones in Synthesis. An Approach to the Synthesis of the Antitumor Sesquiterpene Quadrone, *J. Chem. Soc. Perkin Trans.*, 1:799-809; 1984.

P. Dowd, et al., Free Radical Ring-Expansion Leading to Novel Six- and Seven-Membered Heterocycles, *Tetrahedron*, 47(27):4847-4860, 1991.

M. Greco, et al., Highly Stereoselective Synthesis of Substituted Hydrindanes Related to the Antiepileptic Drug Topiramate, *Tetrahedron Letters*, 33(35):5009-5012, 1992.

M. Moyer. et al., Intramolecular N-H, O-H and S-H Insertion Reactions. Synthesis of Heterocycles from α-Diazo β-Keto Esters, *J. Org. Chem.*, 50:5223-5230, 1985.

M. Wolff, et al., Thia. Steriods. III. Derivatives of 2-Thia-A-nor-5α-androstan-17β-ol As Probes of Steriod-Receptor Interactions, *Journal of Medicinal Chemistry*, 13(3):531-534, 1970.

Dorwald, Side Reactions in Organic Synthesis, *Wiley-VCH, Weinheim*, p. IX of Preface, 2005.

J Massagué, The Transforming Growth Factor-β Family, *Annu Rev Cell Biol.*, 6:597-641, 1990.

A. Roberts, et al., Transforming Growth Factor-βs, *Handbook of Experimental Pharmacology*, 95:419-459, 1990.

S. Wahl, et al., Inflammatory and Immunomodulatory Roles of TGF-β, *Immunol. Today*, 10(8):258-261, 1989.

D. Lawrence, Transforming Growth Factor-β: A General Review, *Euro. Cytokine Network*, 7(3):363-374, 1996.

J. Munger, et al., Latent Transforming Growth Factor-β: Structural Features and Mechanisms of Activation, *Kidney International*, 51:1376-1382, 1997.

J Massagué, Receptors for the TGF-β Family, *Cell*, 69: 1067-1070, 1992.

X Wang, et al., Expression Cloning and Characterization of the TGF-β Type III Receptor, *Cell*, 67:797-805, 1991.

F. Lopez-Casillas, Structure and Expression of the Membrane Proteoglycan Betaglycan, a Component of the TGF-β Receptor System, *Cell*, 67:785-795, 1991.

J. Wrana, et al., TGFβ Signals Through a Heteromeric Protein Kinase Receptor Complex, *Cell*, 71:1003-1014, 1992.

H. Lin, et al., Expression Cloning of the TGF-β Type II Receptor, a Functional Transmembrane Serine/Threonine Kinase, *Cell*, 68:775-785, 1992.

J Massagué, TGF-β Signal Transduction, *Annu. Rev. Biochem.*, 67: 753-791, 1998.

Goodman and Gilman's, The Pharmacological Basis of Therapeutics: Biotransformation of Drugs, $8^{th}$ Ed., *Pergamon Press*, 13-15, 1990.

* cited by examiner

FUSED BICYCLIC INHIBITORS OF HCV

CROSS REFERENCE TO RELATED APPLICATIONS

This application is a U.S. National Phase Application of International Application No. PCT/EP2006/061070, filed Mar. 27, 2006, which claims priority from U.S. Provisional Application Ser. No. 60/665,151, filed Mar. 25, 2005; and U.S. Provisional Application Ser. No. 60/680,405, filed May 12, 2005. The complete disclosures of the aforementioned applications are hereby incorporated herein by reference for all purposes.

FIELD OF THE INVENTION

The invention relates to methods of treating disorders associated with hepatitis C infection. More specifically, it concerns certain fused bicyclic pyrimidine compounds that have an amide-substituted 4-pyridylamine group on the pyrimidine ring that are useful in these methods.

BACKGROUND ART

Transforming growth factor-beta (TGFβ) denotes a superfamily of proteins that includes, for example, TGFβ1, TGFβ2, and TGFβ3, which are pleiotropic modulators of cell growth and differentiation, embryonic and bone development, extracellular matrix formation, hematopoiesis, and immune and inflammatory responses (Roberts and Sporn Handbook of Experimental Pharmacology (1990) 95:419-58; Massague, et al., Ann. Rev. Cell. Biol. (1990) 6:597-646). Other members of this superfamily include activin, inhibin, bone morphogenic protein, and Mullerian inhibiting substance. The members of the TGFβ family initiate intracellular signaling pathways leading ultimately to the expression of genes that regulate the cell cycle, control proliferative responses, or relate to extracellular matrix proteins that mediate outside-in cell signaling, cell adhesion, migration and intercellular communication.

Therefore, inhibitors of the TGFβ intracellular signaling pathway are useful treatments for fibroproliferative diseases. Specifically, fibroproliferative diseases include kidney disorders associated with unregulated TGFβ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fasciitis, morphea, or those associated with the occurrence of Raynaud's syndrome. Lung fibroses resulting from excessive TGFβ activity include adult respiratory distress syndrome, chronic obstructive pulmonary disease (COPD), idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Fibroproliferative conditions can be associated with surgical eye procedures. Such procedures include retinal reattachment surgery accompanying proliferative vitreoretinopathy, cataract extraction with intraocular lens implantation, and post glaucoma drainage surgery.

In addition, members of the TGFβ family are associated with the progression of various cancers. M. P. de Caestecker, E. Piek, and A. B. Roberts, J. National Cancer Inst., 92(17), 1388-1402 (2000). For example, it has been found that TGFβ1 inhibits the formation of tumors, probably by inhibition of the proliferation of nontransformed cells. However, once a tumor forms, TGFβ1 promotes the growth of the tumor. N. Dumont and C. L. Arteaga, Breast Cancer Res., Vol. 2, 125-132 (2000). Thus inhibitors of the TGFβ pathway are also useful for the treatment of many forms of cancer, such as lung cancer, skin cancer, and colorectal cancer. In particular, they are useful to treat cancers of the breast, pancreas, and brain, including glioma.

The compounds of the invention herein are derivatives of pyrimidine having an additional ring fused onto the pyrimidine. PCT publication WO01/47921 describes pyrimidine and triazine compounds that are inhibitors of kinase activities associated with various inflammatory conditions, as opposed to the treatment of fibroproliferative disorders described herein. The above mentioned PCT publication describes the use of the disclosed compounds only for treatment of the inflammatory aspects of certain autoimmune diseases. Further, the compounds described differ from those described herein by virtue of the substitutions required on the pyrimidine nucleus; among other distinctions, the compounds disclosed in the PCT publication do not include phenyl bound directly to the pyrimidine ring.

Related compounds, some of which have the 4-pyridylamine group at C-4 on the pyrimidine, are disclosed in two published U.S. patent applications, publications no. US 2004-0132159-A1 and US 2005/0004143-A1. Those applications, however, disclose a preference for certain electron-donating substituents on the pyridine ring of the 4-pyridylamine group, including alkyl, amine and alkoxy groups, and do not disclose a preferred position for substituents. The present invention provides compounds specifically including a 4-pyridylamine containing an essential carboxamide group attached at position 3 on the pyridine ring.

U.S. Pat. No. 6,476,031 also discloses compounds containing a quinazoline ring, which can be a fused bicyclic derivative of a pyrimidine; it includes compounds where the quinazoline ring is linked to an aryl group at C-4 of the quinazoline. The compounds are reported to act at the TGFβ site, and the compounds can include a 4-pyridylamine group as the aryl group linked to the quinazoline at C-4. However, that patent only discloses that a quinazoline compound linked to a pyridyl that is unsubstituted: it does not disclose any compounds with a 4-pyridyl that includes an amide substituent such as the ones at the 3-position of the 4-pyridyl group in the compounds of the present invention.

DISCLOSURE OF THE INVENTION

The invention is directed to methods, compositions, and novel compounds useful in treating conditions that are characterized by excessive TGFβ activity. These conditions are, most prominently, fibroproliferative diseases, such as conditions associated with hepatitis C virus infection, and certain cancers. However, the conditions for which the compounds and methods are useful include any medical condition characterized by an undesirably high level of TGFβ activity. The compounds of the invention have been found to inhibit TGFβ and are thus useful in treating diseases mediated by the activity of this family of factors. The compounds of the invention are of the formula (I):

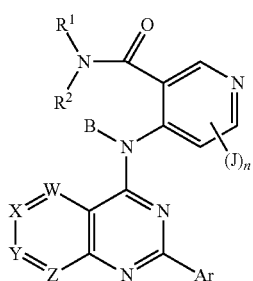

(I)

or a pharmaceutically acceptable salt or prodrug thereof, wherein:

R¹ represents H or OH, or an optionally substituted alkyl, alkoxy, heteroalkyl, amino, acyl, heteroacyl, aryl, arylalkyl, heteroaryl, or heteroarylalkyl group;

R² represents H or optionally substituted alkyl, heteroalkyl, acyl, heteroacyl, aryl, heteroaryl, arylalkyl, or heteroarylalkyl;

B represents H or a C1-C8 acyl group that may be substituted or unsubstituted;

each of W, X, Y and Z is independently C—H, C-J or N, provided that not more than two of W, X, Y and Z represent N;

Ar represents an optionally substituted phenyl ring;

each J independently represents halo, OH, SH, or optionally substituted alkyl, alkenyl, alkynyl, heteroalkyl, heteroalkenyl, heteroalkynyl, aryl, acyl, heteroacyl, or heteroaryl, or $NR^1R^2$, $NO_2$, CN, $CF_3$, COOR, $CONR_2$, or $SO_2R$, wherein each R is independently H or an optionally substituted alkyl, alkenyl, alkynyl, acyl, aryl, heteroalkyl, heteroalkenyl, heteroalkynyl, heteroacyl or heteroaryl group, R¹ and R² of any $NR^1R^2$ can cyclize to form a 3-8 membered ring that can be saturated, unsaturated, or aromatic, and that contains 1-3 heteroatoms selected from N, O and S as ring members, and is optionally substituted; and n is 0-3;

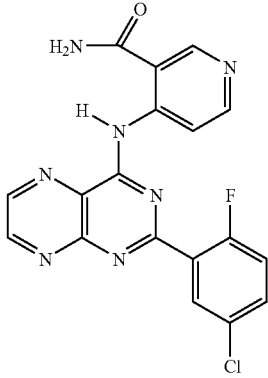

provided the compound is not 4-[2-(5-chloro-2-fluorophenyl)-pteridin-4-ylamino]-nicotinamide:

The invention is also directed to pharmaceutical compositions containing one or more compounds of formula (I) or their pharmaceutically acceptable salts, or prodrug forms thereof, as active ingredients and to methods of treating conditions characterized by an excessive level of TGFβ activity, particularly fibroproliferative conditions, using compounds of formula (I) or compositions containing such compounds.

MODES OF CARRYING OUT THE INVENTION

The compounds of formula (I) are useful in treating conditions which are characterized by an excessive level of TGFβ activity. As used herein, "TGFβ" refers to the superfamily which includes TGFβ1, TGFβ2, and TGFβ3 as well as other members of the family known or which become known in the art such as inhibin, bone morphogenic protein, and the like. One or more of these family members may be more active than desired in the conditions which the compounds of the invention are designed to ameliorate or prevent.

Conditions "characterized by an excessive level of TGFβ activity" include those wherein TGFβ synthesis is stimulated so that TGFβ is present in enhanced amount, and those wherein TGFβ latent protein is undesirably activated or converted to active TGFβ protein, and those wherein TGFβ receptors are upregulated, and those wherein the TGFβ protein shows enhanced binding to cells or extracellular matrix in the location of the disease. Thus, in each case, "excessive level of TGFβ activity" refers to any condition wherein the activity of TGFβ is undesirably high, regardless of the cause and regardless of whether the actual amount or activity of TGFβ present is within a 'normal' range.

Compounds of the present invention moreover show antiviral activity against the hepatitis C virus.

The Invention Compounds

The compounds useful in the invention are fused bicyclic derivatives of pyrimidine containing mandatory substituents at positions corresponding to the 2- and 4-positions of the pyrimidine ring. The bicyclic pyrimidines further have another aromatic ring fused onto the pyrimidine at positions 5 and 6 of the pyrimidine ring. They further include a 4-pyridylamine group at position 4 of the pyrimidine ring and a phenyl group at position 2 of the pyrimidine ring. Optionally, the 4-pyridyl group may be a pyridine-N-oxide. The compounds further include an amide group that is attached at position 3 of the pyridyl ring through its carbonyl carbon. Other substituents may also be included on the pyrimidine, pyridine and phenyl rings and on the aromatic ring fused onto the pyrimidine.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., either as 1-10C or as C1-C10 when the group can contain up to ten carbon atoms. When heteroatoms (N, O and S typically) are allowed to replace carbon atoms as in heteroalkyl groups, for example, the numbers describing the group represent the sum of the number of carbon atoms in the group plus the number of such heteroatoms that are included as replacements for carbon atoms.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond. Alkyl, alkenyl and alkynyl groups are often substituted to the extent that such substitution makes sense chemically. Typical substituents include, but are not limited to, halo, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR, SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl.

"Heteroalkyl", "heteroalkenyl", and "heteroalkynyl" are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is typically connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is typically connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding components of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including halo, C1-C8 alkyl, C2-C8 alkenyl, C2-C8 alkynyl, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl. "Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)- and —$C(Me)_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced accordingly.

"Halo" as used herein includes fluoro, chloro, bromo and iodo. Fluoro and chloro are often preferred.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

The compounds of the invention include a pyrimidine ring, and another six-membered aromatic ring is fused onto the C5 and C6 positions of the pyrimidine. The C2 position of the pyrimidine is occupied by an optionally substituted phenyl group referred to in formula (I) as Ar. The C4 position of the pyrimidine is linked by a nitrogen linker to the C-4 carbon of a pyridine ring. The pyridine is substituted by an amide group at position 3 of the pyridyl ring, and may also be oxidized to its N-oxide. It is optionally substituted by up to three substituents J. In preferred embodiments, the pyridine is not oxidized (m=0).

Substituents J may be present on the pyridine ring in formula (I) at any or all of the positions not otherwise expressly occupied. Thus n in formula (I) can be 0-3. In many preferred embodiments, n is 0; in some embodiments n is 1 or 2.

Typical embodiments of J in formula (I) include the substituents described herein as substituents for an aryl group generally. Preferred embodiments for J include $CF_3$ and CN, as well as halo, C1-C4 alkyl, OR, SR, and $NR_2$, wherein each R is independently H or C1-C4 alkyl or C1-C4 heteroalkyl, where each alkyl or heteroalkyl is optionally substituted with the substituents described above for alkyl groups, and where two R groups on N can optionally cyclize to form a 3-8 membered ring containing one or two heteroatoms selected from N, O and S as ring members. Halo, methyl, methoxy and $CF_3$ are often preferred for each J present.

Ar represents phenyl which may be unsubstituted, but is typically substituted with at least one and preferably two or more substituents selected from the group consisting of halo, C1-C4 alkyl, CN, $CF_3$, OR, $NO_2$, COOR, $CONR_2$, $SO_2R$, $NR_2$, and C1-C8 acyl, where each R is independently H, C1-C4 alkyl, C1-C8 acyl, or C2-C8 heteroacyl. In certain embodiments, Ar is substituted with one or two substituents.

The substituents on Ar may be at any available position on the phenyl ring, but frequently one substituent occupies a ring position adjacent to the atom through which Ar is linked to the pyrimidine ring. For convenience, the position of the phenyl ring that is attached to the pyrimidine ring in formula (I) is referred to as position 1, and other positions on the phenyl ring are numbered relative to that position. Preferred embodiments often have Ar as a phenyl ring that is substituted by at least one halo substituent, which may be at position 2 of that phenyl. A preferred embodiment includes a phenyl ring substituted with two groups, which may both be halogen. 2,5-dihalo phenyl is sometimes specifically preferred, particularly where each halogen is F or Cl; and 2-fluoro-5-chlorophenyl is especially preferred.

The carboxamide on the pyridine ring in formula (I) attaches substituents $R^1$ and $R^2$ to the pyridyl ring specifically at the 3-position. The selection of $R^1$ and $R^2$ is important for its effect on the intrinsic activity of the TGFβ inhibitor compounds, and also can strongly influence their properties related to bioavailability. In some embodiments, $R^1$ is H, OH, or $NH_2$; in other embodiments, $R^1$ is an optionally substituted alkyl, heteroalkyl, alkoxy, amino, acyl, heteroacyl, aryl, arylalkyl, heteroaryl, or heteroarylalkyl group. Typically, $R^1$ is C1-C8 alkoxy, amino, C1-C8 alkyl, C2-C8 heteroalkyl, C6-C10 aryl, C5-C10 heteroaryl, C7-C12-arylalkyl, or C6-C12 heteroarylalkyl, where each of the foregoing groups except H is optionally substituted by the substituents described herein as suitable substituents for such groups. Preferred substituents for the group comprising $R^1$ include halo, OH, $NH_2$, C1-C8 alkyl, C2-C8 heteroalkyl, CN, mono- and di-(C1-C8)-alkyl amines, COOR, $CONR_2$, —NC(O)R, —C(O)$NR_2$, —NRC(O)OR, $SO_2R$, $SO_2NR_2$, and, where available valences permit, =O, =N—OR, =N—CN, and =N—R. Each R in these substituents is independently H, C1-C8 alkyl, C2-C8 heteroalkyl, C6-C10 aryl, C5-C10 heteroaryl, C1-C8 acyl or C2-C8 heteroacyl. Preferred embodiments of $R^1$ include H, C1-C8 alkoxy, $NH_2$, C1-C8 alkyl and C2-C8 heteroalkyl, wherein each alkyl or heteroalkyl is optionally substituted as just described. Typically, not more than one of $R^1$ and $R^2$ is H, so in many embodiments the amide is a secondary or tertiary amide.

In the compounds of formula (I), $R^2$ is H, or an optionally substituted alkyl, acyl, heteroacyl, aryl, heteroaryl, arylalkyl, or heteroarylalkyl group. In some embodiments, $R^2$ is H or a C1-C8 alkyl group, and in others it is a C1-C8 acyl or C2-C8 heteroacyl group or a C7-C12 arylalkyl or C6-C12 heteroarylalkyl group; in each of these embodiments where $R^2$ is other than H, the group represented by $R^2$ is optionally substituted with the substituents described above for $R^1$. More preferred embodiments are those in which $R^2$ represents H or optionally substituted C1-C8 alkyl, and $R^2$=H is often preferred. Preferred substituents for $R^2$ when $R^2$ is other than H include halo, OR, $NR^2$, COOR, and $CONR_2$, where each R is independently H, C1-C4 alkyl, or C1-C4 heteroalkyl.

In some embodiments, $R^1$ and $R^2$ of —C(=O)$NR^1R^2$, $R^1$ can cyclize to form a 3-8 membered ring that can be saturated, unsaturated, or aromatic, and can contain 1-3 heteroatoms selected from N, O and S as ring members, and can be substituted. In some preferred embodiments, $R^1$ and $R^2$ cyclize to form a 3 to 6 membered ring that is saturated or unsaturated and contains either 0 or 1 heteroatom in addition to the N to which $R^1$ and $R^2$ are attached. In other preferred embodiments, $R^1$ and $R^2$ cyclize to form a saturated 6-membered ring containing one heteroatom that is either O or N in addition to the N to which $R^1$ and $R^2$ are attached.

In each case, any ring that is formed by linking $R^1$ and $R^2$ of $NR^1R^2$ is optionally substituted by the substituents that are described herein as suitable substituents for alkyl groups if the ring so formed is non-aromatic, or by the substituents described above for aryl groups if the ring formed by linking $R^1$ and $R^2$ is aromatic. Preferred substituents for the ring formed by $R^1$ and $R^2$ when cyclized include C1-C4 alkyl, OR, $NR_2$, COOR, $CONR_2$, =O, phenyl, and phenyl-$(CH_2)_{1-4}$—, where each R is independently H or C1-C4 alkyl which is optionally substituted with the groups described above as suitable substituents for alkyl groups, and each phenyl is optionally substituted with the substituents described above as suitable for aryl groups.

In certain embodiments, $R^1$ or $R^2$ includes at least one substructure that comprises C=O, S=O, P=O or C=N, and in some embodiments at least one of $R^1$ and $R^2$ comprises —OH or —NH or a tertiary amine that is not acylated so that it can act as a hydrogen bond acceptor. In certain embodiments selected to reduce potential for metabolism of the amide moiety, $R^2$ is H and the amide group shown in formula (1) as —C(=O)—$NR^1R^2$ is not of the formula —C(=O)—NH—$CH_2$—CH(OH)—R where R is H or a hydrocarbyl group that may be substituted. Examples of substructures that may be present in $R^1$ and/or $R^2$ include ethers, amines, alcohols, esters, amides, carbamates, ketones, sulfones, sulfonamides, phosphate esters, polyhydroxylated alkyl or cycloalkyl groups including monosaccharide derivatives, amidines, oximes, guanidines, cyanoguanidines, and the like. In certain embodiments, at least one and preferably two of such polar groups are included in compounds of formula (1).

B in formula (1) can be H or a C1-C8 optionally substituted acyl group. In certain embodiments, B is H. Where B is an acyl group, the compound may serve as a prodrug to release a compound wherein B is H upon metabolic or chemical hydrolysis to cleave off the acyl group.

Each of W, X, Y and Z in formula (I) is independently CH, CJ or N, provided that no more than two of W, X, Y and Z represent N. Thus the combination of W, X, Y and Z, together with the pyrimidine-ring carbon atoms to which W and Z are attached, forms a six membered ring that is aromatic. In some preferred embodiments at least one of W, X, Y and Z is N, and in some of these, at least one of W, Z is N. In certain embodiments Z is N, while W, X and Y each independently represent CH or CJ, and in other embodiments, W and Z are each N and X and Y each represent CH or CJ. Some embodiments have W, X, Y and Z each independently representing CH or C-J, thus forming a carbocyclic ring that, taken with the pyrimidine ring, forms a quinazoline nucleus. Each embodiment of the ring containing W, X, Y and Z is optionally substituted as described herein.

Preferred embodiments include those in which the fused ring containing W, X and Z is phenyl or pyridyl, each of which is optionally substituted as defined above. Pyridyl is sometimes more preferred for this ring, especially when either Z or W represents the pyridyl ring nitrogen.

Another preferred embodiment of the fused ring containing W, X, Y and Z is a pyrazine wherein W and Z are both N, and X and Y each represent CH or CJ.

In some preferred embodiments, the preferred aromatic fused rings mentioned are substituted by at least one group such as halo, optionally substituted C1-C8 alkyl, COOR, $CONR_2$, OR, or $NR_2$, wherein each R is independently H, C1-C8 alkyl or C2-C8 heteroalkyl, and each alkyl or heteroalkyl comprising R is optionally substituted with the substituents defined above for alkyl groups. Thus in these embodiments, at least one of W, X, Y and Z represents C-J, while the others represent N or CH. In such embodiments, it is sometimes preferred that J comprises NH; and in certain embodiments, the NH that J comprises is directly linked to the carbon atom of the group C-J.

In some embodiments of the compounds of formula (1), Y represents C-J, where J comprises an amine, amide or carbamate group. Especially when Z represents N, Y is often C-J, i.e. a substituted carbon. While J in such embodiments can be any of the groups provided herein as suitable substituents for an aromatic ring, in many embodiments, and especially when Z represents N, Y represents C-J wherein J is an amine or a substituted amine group. Typical examples include $NH_2$, C1-C4 monoalkyl amines where the alkyl group may be substituted with, for example, one or two C1-C4 alkoxy, amino, C1-C4 alkylamino or di-(C1-C4)-alkylamino groups. In each case, where a dialkylamine can be present, it can represent a cyclic group such as a pyrrolidine, piperidine, morpholine, and the like, which may be substituted. In other embodiments, when Y represents C-J, J can be an arylalkylamine group such as a benzylamino substituent; and the benzyl group can be substituted with the groups that are described herein as typical for an aryl ring if on the phenyl portion, or with any of the groups suitable for an alkyl group if substitution is on the alkylene portion of the arylalkyl group. Preferred substituents for the phenyl ring of a benzyl in such embodiments include halo, $CF_3$, C1-C4 alkyl, and C1-C4 alkoxy.

As stated above, unless otherwise described, any aryl, alkyl, heteroaryl, heteroalkyl, acyl, heteroacyl, arylalkyl, or heteroarylalkyl group included within a substituent may itself be substituted with the substituents described above as typical for such aryl, alkyl, acyl, or arylalkyl groups. These substituents may occupy all available positions of the group, preferably 1-2 positions, or more preferably only one position.

Where two substituents are present on a single atom, such as but not limited to $NR_2$ of an amine or amide, the two substituents may be linked together to form a ring where this is chemically reasonable. Such rings may be saturated or unsaturated and may be further substituted if substitution is permitted for the substituents linked to form the ring. It is specifically contemplated that $R^1$ and $R^2$ or any two R groups on one N can cyclize to form a 3-8 membered ring that may be saturated or unsaturated, and may include 1-3 heteroatoms selected from N, O and S, and which may be optionally substituted as described for the substituents or R groups being linked to form the ring. Where any of the aryl or cyclic moieties, including those depicted in formula (I) and especially the phenyl moieties, can optionally contain at least two substituents, if those substituents occupy adjacent positions on a ring or they are on a single atom, they may also be linked together to form a 5-7 membered carbocyclic ring or a heterocyclic ring containing 1-3 heteroatoms selected from N, O and S. Examples of such rings include a dioxolane fused to a phenyl ring; oxazole fused to a pyridine ring; an acetonide of a 1,2-diol or a 1,3-diol; and a cyclic ketal.

An embodiment of the present invention relates to the pyrido[2,3-d]pyrimidine compounds of formula (II),

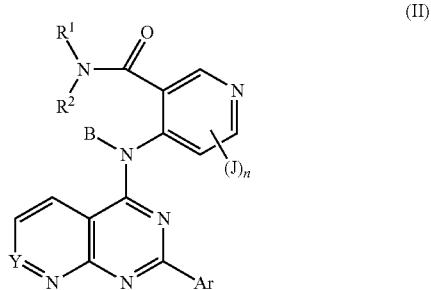

(II)

or a pharmaceutically acceptable salt or prodrug thereof, wherein:

$R^1$ represents H or OH, or an optionally substituted alkyl, alkoxy, heteroalkyl, amino, acyl, heteroacyl, aryl, arylalkyl, heteroaryl, or heteroarylalkyl group;

$R^2$ represents H or optionally substituted alkyl, heteroalkyl, acyl, heteroacyl, aryl, heteroaryl, arylalkyl, or heteroarylalkyl;

B represents H or a C1-C8 acyl group that may be substituted or unsubstituted;

Y is C—H, or C-J;

Ar represents an optionally substituted phenyl ring;

each J independently represents halo, OH, SH, or optionally substituted alkyl, alkenyl, alkynyl, heteroalkyl, heteroalkenyl, heteroalkynyl, aryl, acyl, heteroacyl, or heteroaryl, or $NR^1R^2$, $NO_2$, CN, $CF_3$, COOR, $CONR_2$, or $SO_2R$, wherein each R is independently H or an optionally substituted alkyl, alkenyl, alkynyl, acyl, aryl, heteroalkyl, heteroalkenyl, heteroalkynyl, heteroacyl or heteroaryl group, $R^1$ and $R^2$ of any $NR^1R^2$ can cyclize to form a 3-8 membered ring that can be saturated, unsaturated, or aromatic, and that contains 1-3 heteroatoms selected from N, O and S as ring members, and is optionally substituted; and n is 0-3.

A further embodiment of the present invention relates to the pyrido[2,3-d]pyrimidine compounds of formula (III),

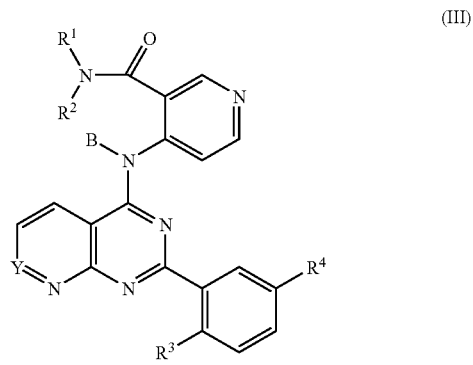

(III)

or a pharmaceutically acceptable salt or prodrug thereof, wherein:

$R^1$ represents H or OH, or an optionally substituted alkyl, alkoxy, heteroalkyl, amino, acyl, heteroacyl, aryl, arylalkyl, heteroaryl, or heteroarylalkyl group;

$R^2$ represents H or optionally substituted alkyl, heteroalkyl, acyl, heteroacyl, aryl, heteroaryl, arylalkyl, or heteroarylalkyl;

B represents H or a C1-C8 acyl group that may be substituted or unsubstituted;

Y is C—H, or C-J;

$R^3$ represents H, or halo;

$R^4$ represents halo;

each J independently represents halo, OH, SH, or optionally substituted alkyl, alkenyl, alkynyl, heteroalkyl, heteroalkenyl, heteroalkynyl, aryl, acyl, heteroacyl, or heteroaryl, or $NR^1R^2$, $NO_2$, CN, $CF_3$, COOR, $CONR_2$, or $SO_2R$, wherein each R is independently H or an optionally substituted alkyl, alkenyl, alkynyl, acyl, aryl, heteroalkyl, heteroalkenyl, heteroalkynyl, heteroacyl or heteroaryl group.

The compounds of the present invention may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, citric, alkylsulfonic, arylsulfonic, and glucuronic acids and the like. If a carboxyl moiety is present on the compounds of the present invention, the compound may also be supplied as a salt with a pharmaceutically acceptable cation, such as sodium, potassium, or an ammonium salt.

The compounds of the present invention may also be supplied in the form of a "prodrug" which is designed to release the compounds the present invention when administered to a subject. Prodrug designs are well known in the art, and depend on the substituents contained in the compounds of the present invention. For example, a substituent containing sulfhydryl could be coupled to a carrier which renders the compound biologically inactive until removed by endogenous enzymes or, for example, by enzymes targeted to a particular receptor or location in the subject. Similarly, ester and amide linkages may be employed to mask hydroxyl, amino, or carboxyl groups on an active molecule within the scope of the invention, and such groups may be enzymatically cleaved in vivo to release the active molecule. In the specific context of formula (1), B can represent an acyl group that is selected for its ability to hydrolyze at a suitable rate in vivo; thus B could be acetyl or formyl, or B—N in formula (1) can be an amide formed from the carboxylate of an amino acid or a dipeptide, each of which would readily hydrolyze from the nitrogen flanked by two heteroaryl rings in formula (1). Accordingly, such amides wherein B is an acyl group are suitable as prodrugs for delivering a compound of formula (1) wherein B is H.

In the event that any of the substituents of the compounds of the present invention contain chiral centers or rotational isomers (atropisomers), as some, indeed, do, the invention includes each stereoisomeric form thereof, both as an isolated stereoisomer and as a component of a mixture of these stereoisomeric forms. Such mixtures of stereoisomers may be racemic or may be enriched in one enantiomer of a pair of enantiomers where a single chiral center is present. Where more than one stereoisomeric center is present, the invention includes mixtures wherein either, neither or each center is enriched in one stereoisomeric form.

Synthesis of the Invention Compounds

A number of synthetic routes may be employed to produce the compounds of the invention. In general, they may be synthesized from conventional starting materials using reactions known in the art. Specific routes and reactions suitable for synthesis of many of the compounds of the invention are described in U.S. Pat. No. 6,476,031, and in published PCT application WO 2004/024159, and in published US application US 2005/0004143 A1, and in published PCT application US2004/032430, each of which is incorporated by reference specifically for its disclosure of such methods. Typically, the fused ring system is constructed from an aryl ring that corresponds to the ring in formula (1) containing W, X, Y and Z; that aryl ring would having an acylating group adjacent to an amine or a leaving group that can be used to introduce an amine. The acylating group of the aromatic ring is used to acylate a phenyl amidine, whose phenyl group corresponds to Ar in formula (1). Cyclization is then effected under known conditions to produce a fused ring system with a 4-hydroxy-pyrimidine. One example of this condensation is illustrated in Scheme 5 below. The hydroxyl group is then converted to a halo (e.g., Cl or I), which is displaced with a 4-aminopyridine derivative, as shown in Scheme 1.

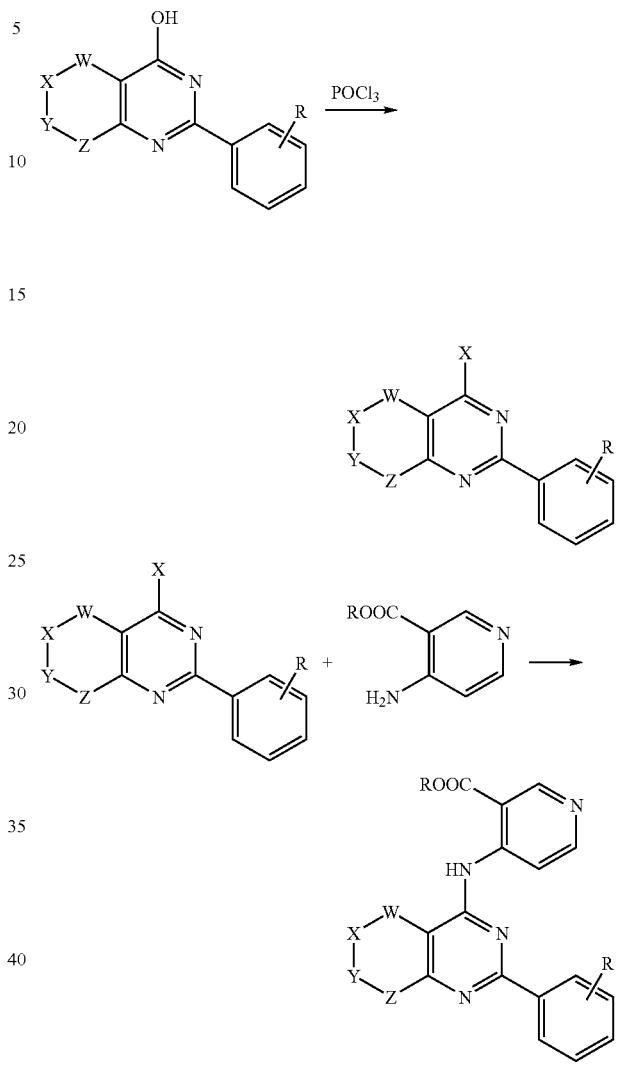

Scheme 1. General method for attaching a 4-aminopyridine to a bicyclic pyrimidine.

X = Cl

Scheme 1 shows how a 4-hydroxy pyrimidine can be converted into a 4-halo pyrimidine, which is then coupled to a 4-aminopyridine. The coupling is done using a palladium catalyst, and may be done with the 4-chloro pyrimidine derivative in some cases, but was done with the 4-iodo derivative in some cases.

The requisite 3-carboxamide group may be present on the 4-aminopyridine when the pyridine is added to the pyrimidine, or the pyridyl group may contain an ester at the 3-position as illustrated in Scheme 1. In that case, the ester can be hydrolyzed with base to form a carboxylic acid after the pyridine group is installed. This carboxylic acid is readily coupled to a wide variety of amine groups by methods well known in the art for forming amide bonds as illustrated in Scheme 2. Because of the wide variety of amines that are available and the generality of this amide formation reaction, this method provides access to a tremendous variety of compounds of the present invention.

Scheme 2. Converting an ester to a carboxamide of formula (I).

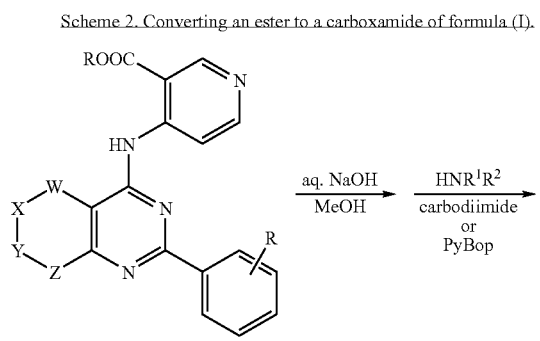

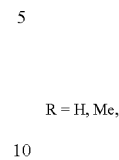 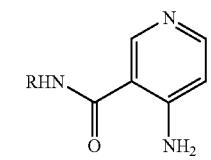

R = H, Me,

Scheme 3a provides a route to prepare the pyridyl nucleus and further substitution thereon. Although the R substituent is exemplified as hydrogen or methyl in the above scheme, it may also include the other substituents as listed under the definitions of $R^1$ and $R^2$.

Scheme 3b. Alternative preperation of 3-carboxamide-4-aminopyridines.

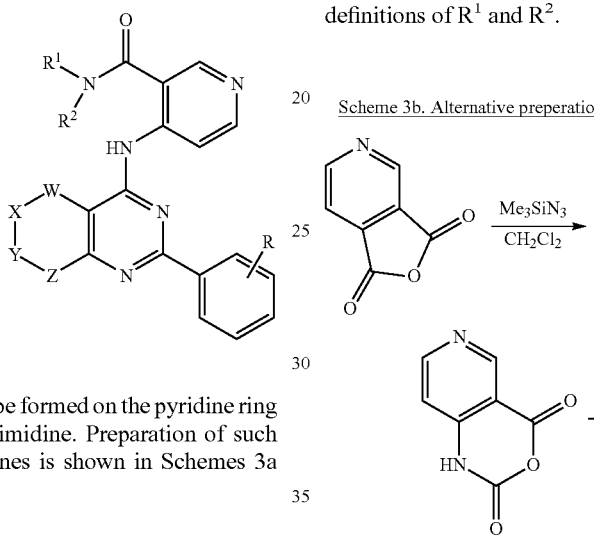

Alternatively, the amide can be formed on the pyridine ring before it is coupled to the pyrimidine. Preparation of such 3-carboxamide-4-amino pyridines is shown in Schemes 3a and 3b.

An alternative way to prepare the 3-carboxamide-4-amino pyridines is illustrated in Scheme 3b using an azaisatoic anhydride.

Numerous methods can be used for making the starting materials required for this approach. For example, in Scheme 5 there is illustrated the preparation of pyrimidines fused to an aromatic ring which can be transformed to end products as described above. the starting amidines can be prepared as illustrated in Scheme 4.

Scheme 3a. Preperation of 3-carboxamide-4-amino pyridines.

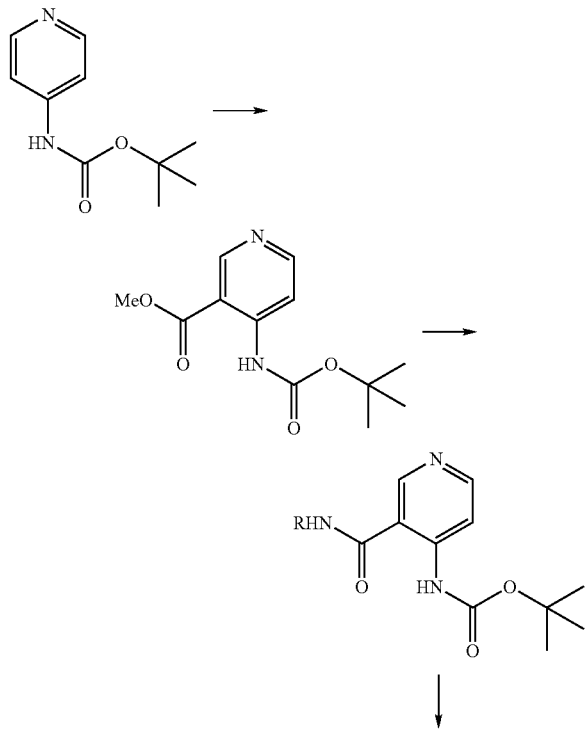

Scheme 4. Preparation of aryl amidines.

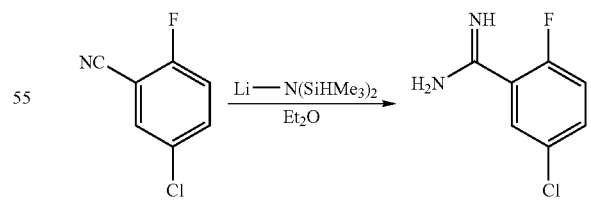

Scheme 5 depicts an overall sequence wherein a fused ring compound of formula (1) wherein Z represents N can be prepared from a suitable pyridine derivative and a phenyl amidine. It further illustrates how a suitably substituted compound of this type can be further modified after it has been synthesized to provide other compounds of formula (1).

Scheme 5. Preperation of pyrimidines fused to an aromatic ring.

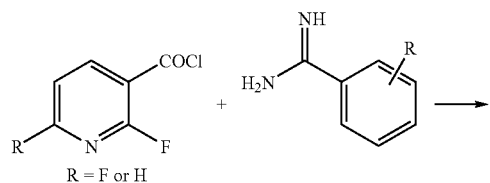

R = F or H

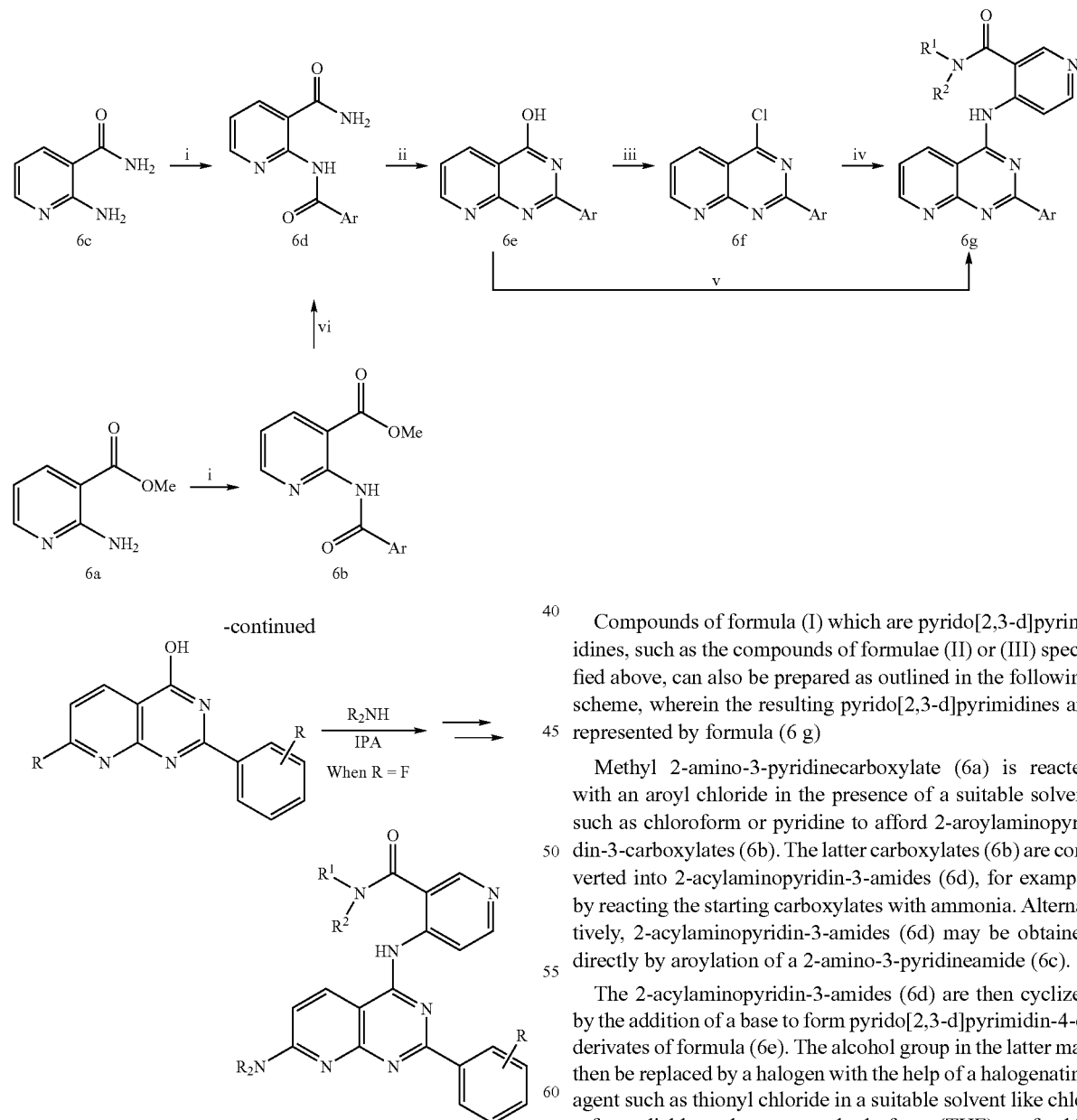

From the intermediates of the process illustrated in Schemes 1-5, other compounds can also be prepared by selection of suitable starting materials. For example, to provide greater variety in the added substituents in Scheme 5, other nucleophiles besides amines can be used to displace the fluoride, as is well known in the art. Furthermore, a protected amine such as bis-(p-methoxybenzyl)amine can be used to displace the fluoride substituent, and the protected amine can later be deprotected and further modified by well-known reactions such as acylation or alkylation to vary the R groups of the added amine substituent on the fused ring. Thus where $R_2NH$ is bis-(p-methoxy-benzyl)amine, $R_2N$ in Scheme 5 represents a bis(p-methoxybenzyl)amine; the p-methoxybenzyl groups can be cleaved by well-known methods such as reduction or treatment with a strong acid, leaving $NH_2$, which can be derivatized by methods well known in the art.

Compounds of formula (I) which are pyrido[2,3-d]pyrimidines, such as the compounds of formulae (II) or (III) specified above, can also be prepared as outlined in the following scheme, wherein the resulting pyrido[2,3-d]pyrimidines are represented by formula (6 g)

Methyl 2-amino-3-pyridinecarboxylate (6a) is reacted with an aroyl chloride in the presence of a suitable solvent such as chloroform or pyridine to afford 2-aroylaminopyridin-3-carboxylates (6b). The latter carboxylates (6b) are converted into 2-acylaminopyridin-3-amides (6d), for example by reacting the starting carboxylates with ammonia. Alternatively, 2-acylaminopyridin-3-amides (6d) may be obtained directly by aroylation of a 2-amino-3-pyridineamide (6c).

The 2-acylaminopyridin-3-amides (6d) are then cyclized by the addition of a base to form pyrido[2,3-d]pyrimidin-4-ol derivates of formula (6e). The alcohol group in the latter may then be replaced by a halogen with the help of a halogenating agent such as thionyl chloride in a suitable solvent like chloroform, dichloroethane or tetrahydrofuran (THF), preferably in the presence of a catalytic amount of dimethylformamide (DMF). Subsequently, the thus obtained intermediates (6f) are converted to the desired end products (6g) by a nucleophilic substitution reaction with an aminopyridinamide of formula

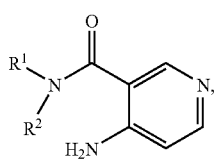

preferably in the presence of a suitable base, e.g. a tertiary amine such as TEA or DIPEA, in an organic solvent such as DCM, THF or DMF.

Alternatively, the 2-aroylaminopyridin-3-amides (6e) may be converted in a one-pot procedure into the pyrido[2,3-d]pyrimidines of formula (II) by reacting (6e) with an aminopyridinamide as specified in the previous paragraph, with a suitable base, in particular a tertiary amine such as TEA or DIPEA, in the presence of benzotriazole-1-yl-oxy-tris-pyrrolidino-phosphonium hexafluorophosphate (PyBOP).

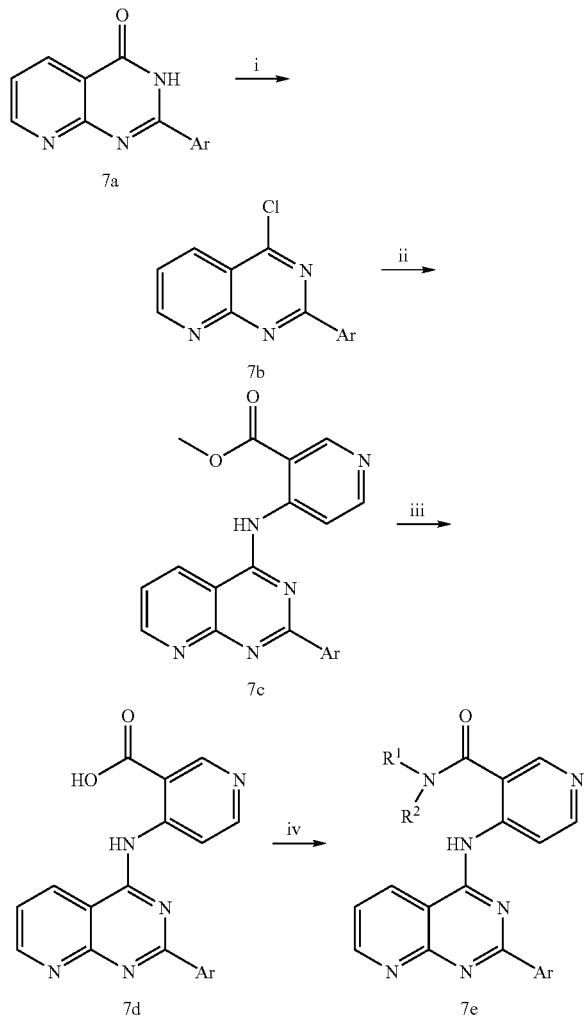

Compounds of formula (I) which are pyrido[2,3-d]pyrimidines, hereafter represented by formula (7e) can also be prepared from a corresponding pyridopyrimidinone (7a) by a halogenation reaction, e.g. with thionyl chloride, in a solvent such as DMF. In a subsequent step, the halo group (in particular chloro) in (7b) is substituted by the aminopyridinamide as described above. The pyrimidine amine in this reaction may be a 4-aminonicotinic acid alkyl ester such as the methyl ester, which is converted after the substitution reaction to the corresponding acid (7d) and then condensed with an amine $HNR^1R^2$ using an amide forming agent such as a carbodiimide or PyBOP.

Where the pyridine N-oxides are desired, the pyridine compounds of the present invention can be oxidized to N-oxides using commonly known oxidation reagents such as, for example, meta-chloroperoxy benzoic acid or peracetic acid.

Administration and Use

The compounds of the invention are useful in treating conditions associated with conditions characterized by excessive TGFβ activity such as fibroproliferation. Thus, the compounds of the invention or their pharmaceutically acceptable salts or prodrug forms are also useful for the manufacture of a medicament for prophylactic or therapeutic treatment of mammals, including humans, in respect of conditions characterized by excessive activity of TGFβ.

TGFβ inhibition activity is useful in treating fibroproliferative diseases, treating collagen vascular disorders, treating eye diseases associated with a fibroproliferative condition, venting excessive scarring, treating neurological conditions and other conditions that are targets for TGFβ inhibitors and in preventing excessive scarring that elicits and accompanies restenosis following coronary angioplasty, cardiac fibrosis occurring after infarction and progressive heart failure, and in hypertensive vasculopathy, and keloid formation or hypertrophic scars occurring during the healing of wounds including surgical wounds and traumatic lacerations.

Neurological conditions characterized by TGFβ production include CNS injury after traumatic and hypoxic insults, Alzheimer's disease, and Parkinson's disease.

Other conditions that are potential clinical targets for TGFβ inhibitors include myelofibrosis, tissue thickening resulting from radiation treatment, nasal polyposis, polyp surgery, liver cirrhosis, and osteoporosis.

Diseases benefited by TGFβ inhibition include cardiovascular diseases such as congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporin, HIV-associated nephropathy, transplant nephropathy, chronic ureteral obstruction; hepatic diseases associated with excessive scarring and progressive sclerosis, including cirrhosis due to all etiologies, disorders of the biliary tree, and hepatic dysfunction attributable to infections such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, fascists, or Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGFβ production or enhanced sensitivity to TGFβ, including states post-traumatic or hypoxic injury, Alzheimer's disease, and Parkinson's disease; diseases of the joints involving scarring sufficient to impede mobility or produce pain, including states post-mechanical or surgical trauma, osteoarthritis and rheumatoid arthritis; and cancer.

Compounds of the invention surprisingly show activity against hepatitis C virus (HCV), more specifically they block replication of HCV. Therefore, compounds of the invention are useful in treating conditions associated with the hepatitis C virus. Thus, compounds of the invention or their pharmaceutically acceptable salts or prodrug forms are also useful in methods for the prophylactic or therapeutic treatment of patients running the risk of developing, or suffering from these conditions. In still a further aspect, the invention provides the compounds of the invention for use as a medicament, in particular for use as a medicament for treating conditions associated with HCV infection. The invention moreover relates to the use for the manufacture of a medicament for the prophylactic or therapeutic treatment of mammals, including humans, running the risk of developing or suffering from conditions associated with hepatitis C virus.

The modulation of the immune and inflammation systems by TGFβ (Wahl, et al., *Immunol. Today* (1989) 10:258-61) includes stimulation of leukocyte recruitment, cytokine production, and lymphocyte effector function, and inhibition of T-cell subset proliferation, B-cell proliferation, antibody formation, and monocytic respiratory burst. TGFβ is a stimulator for the excess production of extracellular matrix proteins, including fibronectin and collagen. It also inhibits the production of enzymes that degrade these matrix proteins. The net effect is the accumulation of fibrous tissue which is the hallmark of fibroproliferative diseases.

TGFβ is active as a homodimer, but is synthesized and secreted from cells as an inactive latent complex of the mature homodimer and proregions, called latency associated protein (LAP). These proteins bind to each other through noncovalent interactions (Lyons and Moses, *Eur. J. Biochem.* (1990) 187: 467). LAP is often disulfide-linked to separate gene products, called latent TGFβ binding proteins or LTBP's. These latent forms provide stability for the mature cytokine and a means for targeting it to the extracellular matrix and cell surfaces (Lawrence, *Eur. Cytokine Network* (1996) 7:363-74). Activation of the latent complex occurs after secretion from cells and is believed to result from the action of proteases, such as plasmin (Munger, et al., *Kidney Intl.* (1997) 51:1376-82), on LAP, thrombospondin-1 binding (Crawford, et al., *Cell* (1998) 93:1159-70), and binding to the integrin v6 (Munger, et al., *Cell* (1999) 319-28).

Other than αvβ there is a variety of cell surface proteins/receptors that transduce the signals initiated by binding of the active TGFβ ligand to its receptors. These include types I, II, III, IV, and V. Type IV is present only in the pituitary gland while the others are ubiquitous. The binding affinities among the three isoforms for the type I and II receptors differ such that these two receptors bind TGFβ1 and TGFβ3 more tightly than TGFβ2 (Massague, *Cell* (1992) 69:1067-70).

The type IV receptor or endoglin has a similar isoform binding profile in contrast to the type III receptor, betaglycan, which binds equally well to all three isoforms (Wang, et al., *Cell* (1991) 67:797-805; Lopez-Casillas, *Cell* (1991) 67:785-95). The type V receptor binds to IGFBP-3 and is thought to have an active kinase domain similar to the type I and II receptors. Cloning of the type I and type II receptors demonstrated the existence of cytoplasmic serine/threonine kinase domains (Wrana, et al., *Cell* (1992) 71:1003-14; Lin, et al., *Cell* (1992) 68:775-85; Ibid. 71:1069; Massague, *Cell* (1992) 69:1067-70). Initiation of the TGFβ signaling pathway results from the binding of the TGFβ ligand to the extracellular domain of the type II receptor (Massague, *Ann. Rev. Biochem.* (1998) 67:753-91). The bound receptor then recruits type I receptor into a multimeric membrane complex, whereupon the constitutively active type II receptor kinase phosphorylates and activates type I receptor kinase. The function of the type I receptor kinase is to phosphorylate a receptor-associated co-transcription factor, smad-2/3, thereby releasing it into the cytoplasm where it binds to smad-4. This smad complex translocates into the nucleus, associates with a DNA-binding cofactor, such as Fast-1, binds to enhancer regions of specific genes, and activates transcription. The expression of these genes leads to the synthesis of cell cycle regulators that control proliferative responses or extracellular matrix proteins that mediate outside-in cell signaling, cell adhesion, migration, and intercellular communication.

The manner of administration and formulation of the compounds useful in the invention and their related compounds will depend on the nature of the condition, the severity of the condition, the particular subject to be treated, and the judgment of the practitioner; formulation will depend on mode of administration. As the compounds of the invention are small molecules, they are conveniently administered by oral administration by compounding them with one or more suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the routine oral dosage will utilize 0.001-100 mg/kg total body weight, preferably from 0.01-50 mg/kg and more preferably about 0.01 mg/kg-10 mg/kg. Dosages will typically be administered at least once per day, but the dose regimen will vary, depending on the conditions being treated and the judgment of the practitioner. For some uses, the compounds or compositions may be administered several times per day and for other uses they may be administered less frequently than once per day.

It should be noted that the compounds of the present invention can be administered as individual active ingredients, or as mixtures of several embodiments of this formula. The compounds of the invention may be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As indicated above, although the compounds of the invention may be used in humans, they are also available for veterinary use in treating animal subjects.

Compounds of the invention, in particular the compounds of formula (II) or (III), show anti-viral properties and in particular are active against HCV. Compounds of the invention therefore are useful in the treatment of individuals infected by HCV and for the prophylaxic treatment of individuals at risk of being infected. Compounds of the present invention may also find use in the treatment of warm-blooded animals infected with flaviviruses. Conditions which may be prevented or treated with compounds of the present invention, are conditions associated with HCV and other pathogenic flaviviruses, such as Yellow fever, Dengue fever (types 1-4), haemorraghic fever, encephalitis (St. Louis encephalitis, Japanese encephalitis, Murray valley encephalitis), West Nile virus and Kunjin virus. Conditions associated with HCV include progressive liver fibrosis, inflammation and necrosis leading to cirrhosis, end-stage liver disease, and HCC.

Thus in another aspect, the present invention provides a method of treating HCV infection in a warm-blood animal, in particular a human, said method comprising the administration of an effective amount of a compound of formula (I), and in particular a compound of formula (II) or (III), as specified herein. Or, this invention provides a method for treating a warm-blooded animal, in particular a human, from conditions associated with HCV infection said method comprising the administration of an effective amount of a compound of formula (I) and in particular a compound of formula (II) or (III), as specified herein.

Compounds of the invention and in particular compounds of formula (II) or (III) or any subgroup thereof, may therefore be used as medicines against the above-mentioned conditions. Said use as a medicine or method of treatment comprises the systemic administration to HCV-infected subjects of an amount effective to combat the conditions associated with HCV and other pathogenic flaviviruses. Consequently, the compounds of the present invention can be used in the manufacture of a medicament useful for treating conditions associated with HCV and other pathogenic flaviviruses.

In an embodiment, the invention relates to the use of a compound of the invention and in particular a compound of formula (II) or (III) or any subgroup thereof as defined herein in the manufacture of a medicament for treating or combating infection or disease associated with HCV infection in a mammal. The invention also relates to a method of treating a flaviviral infection, or a disease associated with flavivirus infection comprising administering to a mammal in need thereof an effective amount of a compound of the invention and in particular of a compound of formula (II) or (III) or a subgroup thereof as defined herein.

In another embodiment, the present invention relates to the use of a compound of the invention and in particular a compound formula (II) or (III) or any subgroup thereof as defined herein, for the manufacture of a medicament useful for inhibiting viral activity in a mammal infected with flaviviruses, in particular with HCV.

In another embodiment, the present invention relates to the use of formula (II) or (III) or any subgroup thereof as defined herein for the manufacture of a medicament useful for inhibiting viral activity in a mammal infected with flaviviruses, or in particular infected with HCV, wherein said flaviviruses or HCV is inhibited in their or its replication.

The invention furthermore relates to combinations of a compound of this invention, in particular a compound of formula (II) or (III) as specified herein, and another anti-HCV compound. The invention also provides methods of treating warm-blooded animals, in particular humans, suffering from HIV infection or conditions associated with HCV infection, as mentioned above, said methods comprising the administration of a combination of a compound of this invention, in particular a compound of formula (II) or (III) as specified herein, and another anti-HCV compound. Anti-HCV compounds comprise, for instance, interferon-α (IFN-α), pegylated interferon-α and/or ribavirin. The combinations of a compound of the invention and in particular of a compound of formula (II) or (III), with another anti-HCV compound can be used as a medicine in a combination therapy. The term "combination therapy" relates to a product containing (a) a compound of the invention, in particular a compound of formula (II) or (III), and (b) another anti-HCV compound, as a combined preparation for simultaneous, separate or sequential use in treatment of HCV infections, in particular, in the treatment of infections with HCV type 1. Thus, to combat or treat HCV infections, the compounds of the invention, and in particular compounds of formula (II) or (III) may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of the invention, in particular a compound of formula (II) or (III) or any subgroup thereof as defined above, for the manufacture of a medicament useful for inhibiting HCV activity in a mammal infected with HCV viruses, wherein said medicament is used in a combination therapy, said combination therapy preferably comprising a compound of formula (II) or (III) and (pegylated) IFN-α and/or ribavirin, and possibly an anti-HIV compound.

It will be appreciated by the person skilled in the art that the compounds of the invention may be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

The following examples are intended to illustrate, but not to limit, the invention. They represent examples of the methods and intermediates suitable for preparing compounds of the present invention. Other combinations and modifications of these reactions and others well known in the art can be utilized to provide many other compounds of the present invention.

Example 1

Synthesis of Amidines

Amidine intermediates suitable for preparing certain compounds of formula (I) can be synthesized using lithium bis(trimethylsilyl)amide:

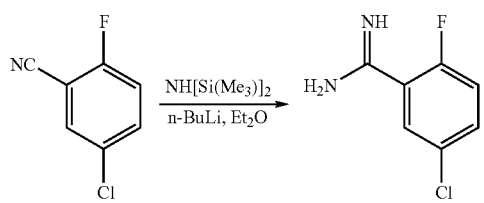

To a stirred 0° C. solution of 1,1,1,3,3,3-Hexamethyldisilazane (63 mL, 0.3 mol) in dry diethyl ether was added dropwise n-Butyl lithium (2M in hexanes, 150 mL, 0.3 mol). A white suspension formed, to which was added 2-Fluoro-5-chlorobenzonitrile (21.0 g, 0.14 mol) over 5 min. The resultant orange mixture was allowed to warm to r.t. and stirred for 2 h. The mixture was cooled to 0° C. and the reaction quenched by the addition of 3M HCl (aq.) (240 mL). The mixture was stirred for 0.5 h before water (600 mL) was added. The purple organic layer was discarded and the aqueous layer basified to pH 14 with satd. NaOH (aq.). The aqueous layer was extracted with CHCl$_3$ (5×100 mL) and the organic extracts dried over Na$_2$SO$_4$. Evaporation yielded the desired product as a yellow solid (16.2 g, 73% yield).

Example 2

Synthesis of 4-[2-(5-Chloro-2-fluoro-phenyl)-7-(2-dimethylamino-ethylamino)-pyrido-[2,3-d]pyrimidin-4-ylamino]-nicotinic acid

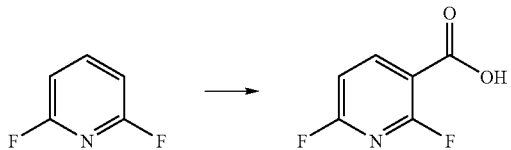

2,6-Difluoro-nicotinic acid. To a solution of anhydrous THF (50 mL) and diisopropyl amine (14.02 mL) cooled to −78° C. was added n-BuLi (2M, 50 mL). The mixture was allowed to warm to 0° C. for 30 min and was cooled to −78° C. 2,6-Di-fluoropyridine (11.5 g) dissolved in THF (200 mL) was added to the LDA mixture at −78° C. The mixture stirred at −78° C. for 2 h, the ice bath was removed and the mixture stirred at 0° C. for 10 min. The mixture was cooled to −78° C. and a stream of CO$_2$(g) was passed through the mixture for 15 minutes until the mixture became clear. The mixture stirred for 1 h at −78° C. and H$_2$O (100 mL) was added. The ice bath was removed and the mixture warmed to rt. The THF was removed under reduced pressure and H$_2$O (200 mL) was added followed by acidification to pH 3.5 with HCl. The mixture was extracted with EtOAc (3×150 mL). The combined organics were dried over MgSO$_4$, filtered and evaporated to afford the 2,6-difluoronicotinic acid (9.4 g). Material used without further purification.

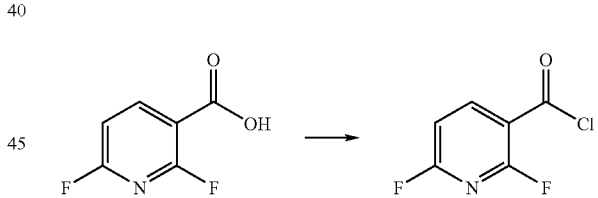

2,6-Difluoro-nicotinoyl chloride. A mixture of 2,6-difluoronicotinic acid (6.2 g), thionyl chloride (15 mL) and CH$_2$Cl$_2$ (100 mL) was heated to reflux for 3 h. The mixture was evaporated to dryness, CH$_2$Cl$_2$, was added and evaporated to dryness to afford 1.1 g of the 2,6-difluoronicotinic acid chloride. This material used without further purification.

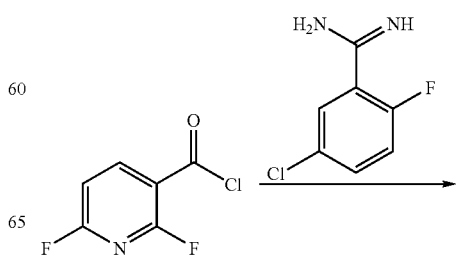

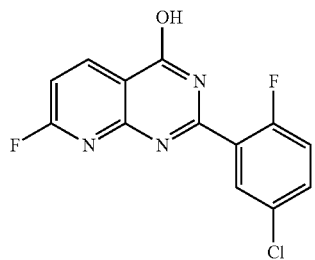

2-(5-Chloro-2-fluoro-phenyl)-7-fluoro-pyrido[2,3-d]pyrimidin-4-ol. To a mixture of 2,6-difluoronicotinic acid chloride (6.4 g), dissolved in acetonitrile (200 mL) was added 2-fluoro-5-chlorobenzamidine (6.73 g) and diisopropyl ethyl amine (24 mL). The mixture was heated to reflux for 2 h and cooled to room temperature. The mixture was concentrated under reduced pressure. The precipitate was filtered and washed with ether and dried under reduced pressure to afford the 2-(5-chloro-2-fluoro-phenyl)-7-fluoro-pyrido[2,3-d]pyrimidin-4-ol that was used without further purification.

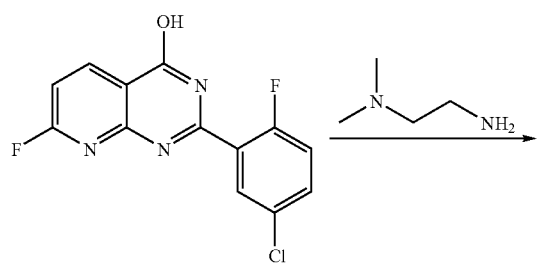

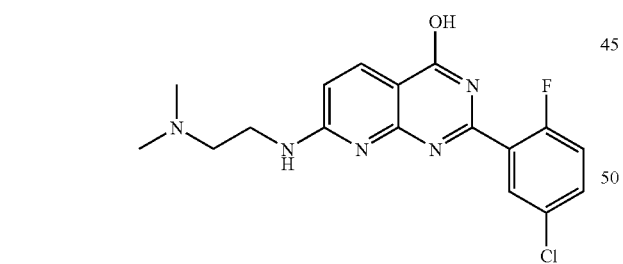

2-(5-Chloro-2-fluoro-phenyl)-7-(2-dimethylamino-ethylamino)-pyrido[2,3-d]pyrimidin-4-ol. To a solution of 2-(5-chloro-2-fluoro-phenyl)-7-fluoro-pyrido[2,3-d]pyrimidin-4-ol (0.16 g) in iso-propanol (20 mL) was added 2-dimethylamino-ethylamine (0.051 g). The mixture was heated to reflux for 1 h and the mixture was reduced in volume to afford a precipitate that was filtered and dried. The isolated solid, 2-(5-Chloro-2-fluoro-phenyl)-7-(2-dimethylamino-ethylamino)-pyrido[2,3-d]pyrimidin-4-ol, was used without further purification.

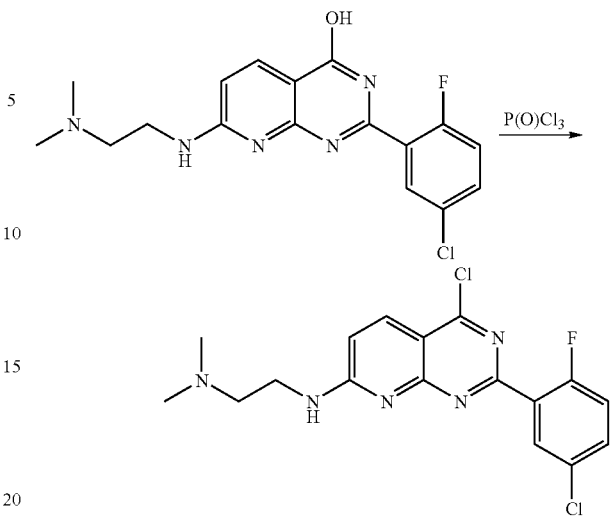

N'-[4-Chloro-2-(5-chloro-2-fluoro-phenyl)-pyrido[2,3-d]pyrimidin-7-yl]-N,N-dimethyl-ethane-1,2-diamine. The 2-(5-Chloro-2-fluoro-phenyl)-7-(2-di-methylamino-ethylamino)-pyrido[2,3-d]pyrimidin-4-ol (0.18 g) was dissolved in P(O)Cl$_3$ (10 mL) and heated to reflux for 2 hr. The mixture was reduced in volume and NaHCO$_3$ (sat aq) was added. The mixture was extracted with CH$_2$Cl$_2$ (×3). The extracts were combined and dried over MgSO4, filtered and evaporated to dryness to afford N'-[4-Chloro-2-(5-chloro-2-fluoro-phenyl)-pyrido[2,3-d]pyrimidin-7-yl]-N,N-dimethylethane-1,2-diamine.

4-[2-(5-Chloro-2-fluoro-phenyl)-7-(2-dimethylamino-ethylamino)-pyrido[2,3-d]-pyrimidin-4-ylamino]-nicotinic acid methyl ester. Crude imino halide, N'-[4-Chloro-2-(5-chloro-2-fluoro-phenyl)-pyrido[2,3-d]pyrimidin-7-yl]-N,Ndimethyl-ethane-1,2-diamine (0.58 g) dissolved in dioxane (80 ml) was added Pd(OAc)$_2$ (0.077 g) followed by BINAP (0.115 g), 4-amino-pyridyl-3-carboxylate (0.232 g) and C$_{S2}$CO$_3$ (0.748 g). The reaction mixture was heated to 80° C. for 15 h. The reaction mixture was cooled to r.t. and filtered through diatomaceous earth and the crude material was purified by silica gel flash column chromatography (3:2/ethyl acetate:hexane) to give 4-[2-(5-Chloro-2-fluoro-phenyl)-7-(2-dimethylamino-ethylamino)-pyrido[2,3-d]-pyrimidin-4-ylamino]-nicotinic acid methyl ester (0.300 g).

4-[2-(5-Chloro-2-fluoro-phenyl)-7-(2-dimethylamino-ethylamino)-pyrido[2,3-d]pyrimidin-4-ylamino]-nicotinic acid. To a suspension of the ester, 4-[2-(5-Chloro-2-fluoro-phenyl)-7-(2-dimethylamino-ethylamino)-pyrido[2,3-d]pyrimidin-4-ylamino]-nicotinic acid methyl ester (0.300 g) in MeOH (20 ml) was added a 1N NaOH (aq) (1.0 ml) and the reaction mixture was heated to reflux for 2 h. The solution was cooled to rt and concentrated in vacuo. Water (50 ml) was added to the crude material and the aqueous layer was acidified with HCl (1 N) and the mixture was placed in the freezer. The solid was filtered, washed with water and dried to give 4-[2-(5-Chloro-2-fluorophenyl)-7-(2-dimethylamino-ethylamino)-pyrido[2,3-d]pyrimidin-4-ylamino]-nicotinic acid as a cream colored solid. This material was used without further purification.

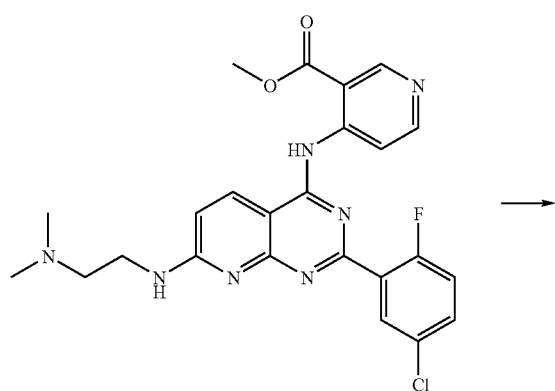

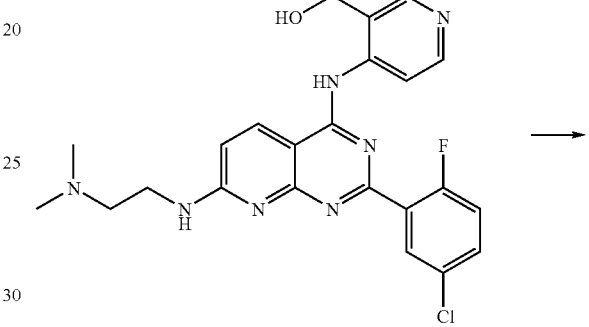

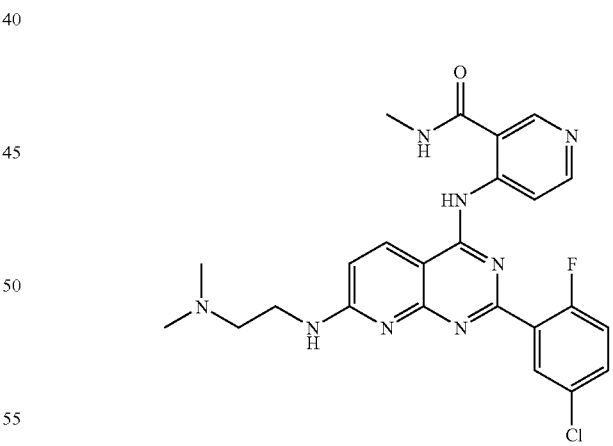

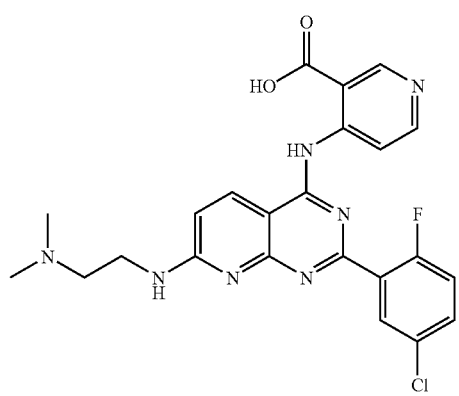

4-[2-(5-Chloro-2-fluoro-phenyl)-7-(2-dimethylamino-ethylamino)-pyrido[2,3-d]pyrimidin-4-ylamino]-N-methyl-nicotinamide. To a suspension of substituted nicotinic acid, 4-[2-(5-Chloro-2-fluoro-phenyl)-7-(2-dimethylamino-ethylamino)-pyrido[2,3-d]pyrimidin-4-ylamino]-nicotinic acid (0.030 g) in dry DMF (1 ml) was added Carbonyldiimidazole (0.020 g) followed by methylamine (156 uL, 2 M solution if THF). The reaction mixture was stirred at room temperature for 16 h. The crude residue was purified by preparative HPLC (Acetonitrile/water 5% to 95% gradient) to give 4-[2-(5-

Chloro-2-fluoro-phenyl)-6,7-dihydro-5H-cyclopentapyrimidin-4-ylamino]-N-methyl-nicotinamide (280 mg, 68%) as a white solid.

Example 3

Synthesis of 4-[7-Amino-2-(5-chloro-2-fluoro-phenyl)-pyrido[2,3-d]pyrimidin-4-yl-amino]-N-methyl-nicotinamide

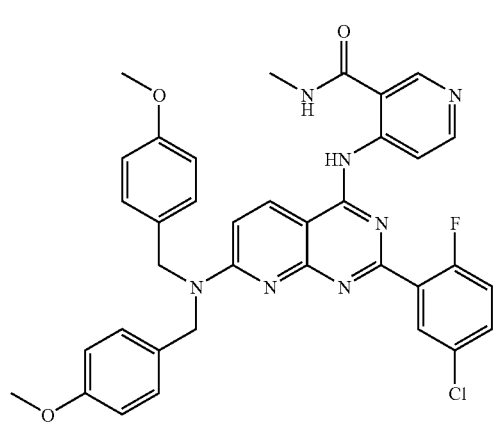

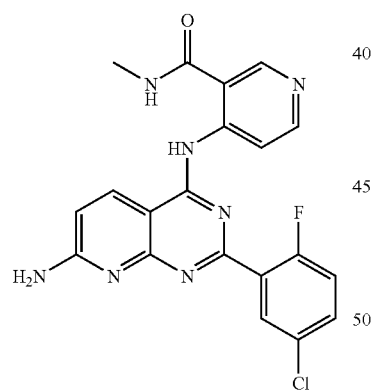

4-[7-Amino-2-(5-chloro-2-fluoro-phenyl)-pyrido[2,3-d]pyrimidin-4-ylamino]-N-methyl-nicotinamide. Using the methods descried in Example 2, the protected amine compound, 4-[7-[Bis-(4-methoxy-benzyl)-amino]-2-(5-chloro-2-fluorophenyl)-pyrido[2,3-d]pyrimidin-4-ylamino]-N-methyl-nicotinamide, was prepared. The two methoxybenzyl protecting groups were then removed as follows. A suspension of 4-[7-[Bis-(4-methoxy-benzyl)-amino]-2-(5-chloro-2-fluoro-phenyl)-pyrido[2,3-d]pyrimidin-4-ylamino]-N-methyl-nicotinamide (1.96 g; 3.14 mmol) in neat trifluoroacetic acid (30 mL) was heated to 40° C. for 30 h. The reaction mixture was evaporated to dryness and purified by silica gel chromatography (dichloromethane/EtOAc gradient 95/5 to 5/95) to afford 4-[7-Amino-2-(5-chloro-2-fluoro-phenyl)-pyrido[2,3-d]pyrimidin-4-ylamino]-N-methyl-nicotinamide (0.78 g).

Example 4

Preparation of 4-[2-(5-Chloro-2-methylamino-phenyl)-pyrido[2,3-d]pyrimidin-4-ylamino]-N-methyl-nicotinamide

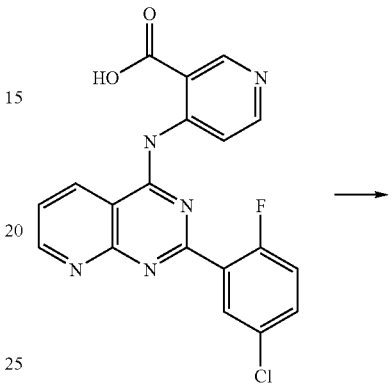

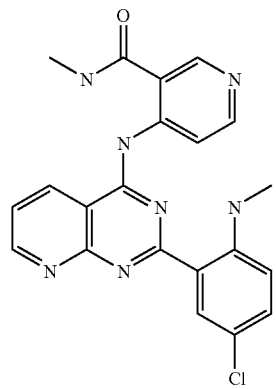

4-[2-(5-Chloro-2-methylamino-phenyl)-pyrido[2,3-d]pyrimidin-4-ylamino]-N-methyl-nicotinamide. Carbonyldiimidazole (180 mg, 1.11 mmol) was added to a stirred suspension of the acid, 4-[2-(5-Chloro-2-fluoro-phenyl)-pyrido[2,3-d]pyrimidin-4-ylamino]-nicotinic acid (240 mg, 0.56 mmol) in dry DMF (15 ml). The reaction was heated to 60° C. for 2 hours under nitrogen. The reaction was cooled to room temperature and MeNH$_2$ (2M in THF, 5 equivalents) was added and the reaction stirred for 18 hours. The reaction mixture was partitioned between CHCl$_3$ (50 mL) and water (50 mL). The organic layer was further washed with water (3×50 mL). The product precipitated out of the CHCl$_3$ solution and was filter to give compound 4-[2-(5-Chloro-2-methylamino-phenyl)-pyrido[2,3-d]pyrimidin-4-ylamino]-N-methyl-nicotinamide (47 mg, 19% yield).

Example 5

Synthesis of 4-[2-(5-Chloro-2-fluoro-phenyl)-pyrido[2,3-d]pyrimidin-4-ylamino]-N-methyl-nicotinamide

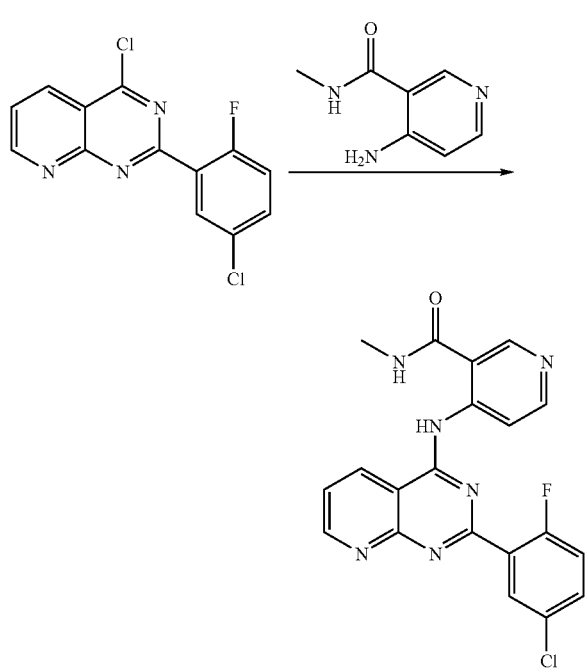

4-[2-(5-Chloro-2-fluoro-phenyl)-pyrido[2,3-d]pyrimidin-4-ylamino]-N-methylnicotinamide. This compound was prepared by the synthetic method described in Example 2 above.

Example 6

Synthesis of 4-Aminopyridinyl-3-carboxamides

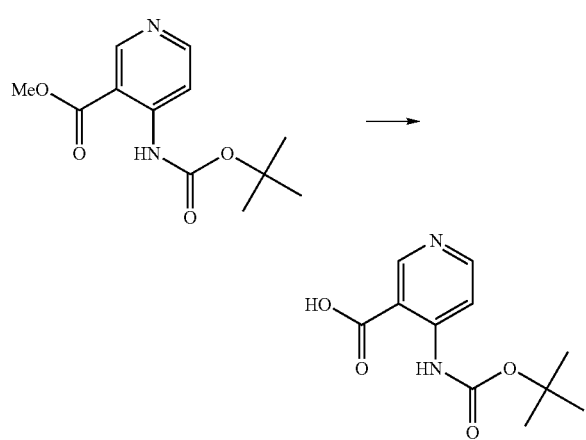

4-tert-Butoxycarbonylamino-nicotinic acid. To a solution of 4-tert-butoxycarbonylamino-nicotinic acid methyl ester (6.02 g, 23.86 mmol) in dioxane (100 mL) was added aq. sodium hydroxide (0.970 N solution, 28.05 mL, 27.20 mmol). The solution was heated to 60° C. for 1 hr then cooled. Aqueous hydrochloric acid (1.03 µM solution, 26.99 mL, 27.20 mmol) was added and the mixture was extracted with chloroform (5×100 mL). The extracts were dried (MgSO$_4$), filtered, and evaporated to give 4-tert-Butoxycarbonylamino-nicotinic acid, a cream solid (4.70 g, 83% yield).

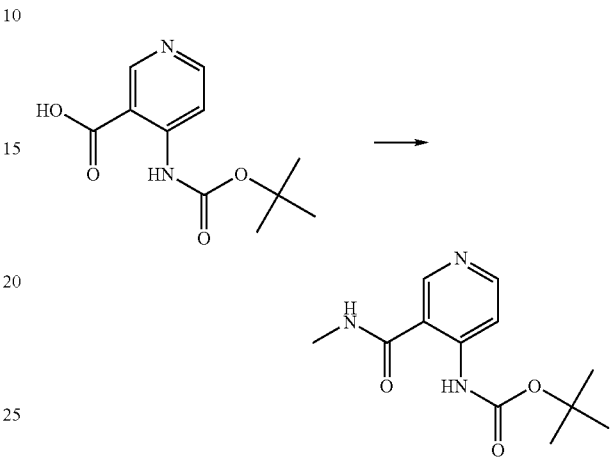

(3-(N-methylaminocarbonyl)-pyridin-4-yl)-carbamic acid tert-butyl ester. The acid, 4-tert-Butoxycarbonylamino-nicotinic acid (1.0 g, 4.20 mmol) was suspended in dry DMF (50 mL) followed by carbonyl-diimidazole (CDI, 1.36 g, 8.40 mmol). The mixture was heated to 60° C. for 1 h, then cooled. Methyl amine in THF was added to the solution followed by evaporation of the mixture. The residue was dissolved in water (20 mL)/chloroform (50 mL) and shaken then the layers separated. The aqueous layer was extracted further with chloroform (3×50 mL) and the combined organic extracts dried (MgSO$_4$) and evaporated to give a yellow oily solid. Silica gel chromatography (CH$_2$Cl$_2$, 0-15% MeOH gradient) gave the desired product, (3-(N-methylaminocarbonyl)-pyridin-4-yl)-carbamic acid tert-butyl ester, as a yellow solid.

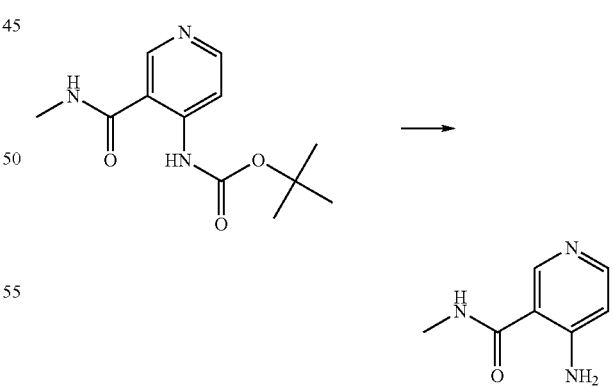

4-Amino-3-(N-methylaminocarbonyl)-pyridine. The amide, (3-methylcarboxymethylamido-pyridin-4-yl)-carbamic acid tert-butyl ester was treated with trifluoroacetic acid (TFA, 20 mL) and stirred at r.t. for 45 min, then evaporated to give the desired amine, 4-Amino-N-methyl-nicotinamide, as its TFA salt (892 mg, 85% yield from 4-tert-butoxycarbonylamino-nicotinic acid methyl ester).

Example 7

Synthesis of 2-(4-Fluorophenyl)-4-chloro Pteridine

Compounds of formula (I) wherein W and Z each represent N can be made by the methods in the examples above, using a 2-phenyl-4-chloro pteridine intermediate. Such intermediates can be prepared using the following methods.

Pyridine (2.1 mL, 0.025 mol) was added to methyl 3-amino-2-pyrazine carboxylate Ia (3 g, 0.020 mol) in dry $CHCl_3$ (50 mL) and stirred for 5 minutes under nitrogen at room temperature. 4-fluorobenzoyl chloride (3.5 mL, 0.029 mol) was added slowly to the reaction mixture. The mixture was stirred for 18 hours under nitrogen. The reaction mixture was washed with 5% $Na_2CO_3$ solution (2×200 mL), water (2×200 mL), brine (2×200 mL), dried ($MgSO_4$) and the solvent was removed in vacuo. The desired product acylated aminopyrazine was obtained by re-crystallization from ethyl acetate (1.6 g, 30% yield). EIMS: M+ 275.

$NH_4OH$ (28% $NH_3$ in $H_2O$, 10 mL) was added to a stirred suspension of the amide Ib (0.69 g) in EtOH (30 mL) and stirred for 1 hr. 10M NaOH (2 mL) was added and refluxed for 1 hr. The solvent was removed in vacuo. The solid was re-suspended in water and acidified with 4M HCl until the solution was at pH 1. The product, 4-hydroxy-2-(4-fluorophenyl) pteridine, was filtered and washed with water and acetone and dried in vacuo at 45° C. for 18-24 hours (0.25 g, 42% yield). EIMS: M+=242.

Thionyl chloride (0.4 mL, 0.005 mol) was added to the stirred suspension of the hydroxypteridine from the preceding step (0.25 g, 0.001 mol) in dry $CHCl_3$ (15 mL) and dry DMF (0.5 mL). The reaction mixture was refluxed under nitrogen for 1 hour. The solvent was removed in vacuo to give the 2-(4-fluorophenyl)-4-chloro pteridine as a solid, which was dried on the high vacuum pump for 1 hour and directly used in the next reaction, coupling with a suitably substituted 4-aminopyridine.

Example 8

Activity of the Invention Compounds

The compounds of the invention were tested for their ability to inhibit TGFβ by a TGFβ $R^1$ autophosphorylation protocol. This was conducted as follows: Compound dilutions and reagents were prepared fresh daily. Compounds were diluted from DMSO stock solutions to 2 times the desired assay concentration, keeping final DMSO concentration in the assay less than or equal to 1%. TGFβ $R^1$ was diluted to 4 times the desired assay concentration in buffer+DTT. ATP was diluted into 4× reaction buffer, and gamma-$^{33}$P-ATP was added at 60 uCi/mL.

The assay was performed by adding 10 ul of the enzyme to 20 ul of the compound solution. The reaction was initiated by the addition of 10 ul of ATP mix. Final assay conditions included 10 uM ATP, 170 nM TGFβ R1, and 1M DTT in 20 mM MOPS, pH7. The reactions were incubated at room temperature for 20 minutes. The reactions were stopped by transferring 23 ul of reaction mixture onto a phosphocellulose 96-well filter plate, which had been pre-wetted with 15 ul of 0.25M $H_3PO_4$ per well. After 5 minutes, the wells were washed 4× with 75 mM $H_3PO_4$ and once with 95% ethanol. The plate was dried, scintillation cocktail was added to each well, and the wells were counted in a Packard TopCount microplate scintillation counter.

The compounds in Table 1 were prepared by the methods set forth herein. The compounds were characterized at least by LC-mass spectrometry. For each compound in the Table, the product observed by LC (liquid chromatography) provided the molecular ion expected for the desired product; the characteristic ion is listed in Table 1 for each compound, along with the retention time from the LC. These compounds provide, in this assay, $IC_{50}$ values in the range of 0.01-12 micromolar.

TABLE 1

| Compound No. | Structure | m/z (M + H$^+$), retention time (min) | $IC_{50}$ for Kinase Inhibition |
|---|---|---|---|
| 1 | 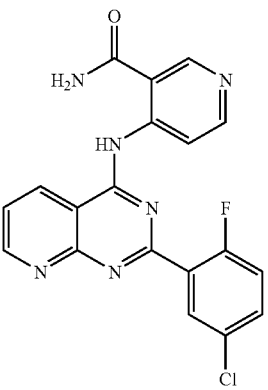<br>AutoNom Name:<br>4-[2-(5-Chloro-2-fluoro-phenyl)-pyrido[2,3-d]pyrimidin-4-ylamino]-nicotinamide | 395.0, 2.040$^a$ | 0.02 |

TABLE 1-continued

| Compound No. | Structure | m/z (M + H⁺), retention time (min) | IC$_{50}$ for Kinase Inhibition |
|---|---|---|---|
| 2 | 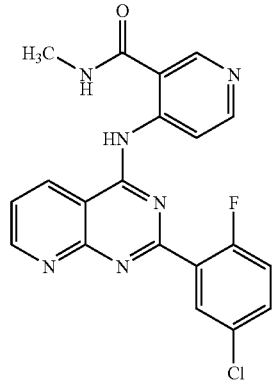 AutoNom Name: 4-[2-(5-Chloro-2-fluoro-phenyl)-pyrido[2,3-d]pyrimidin-4-ylamino]-N-methyl-nicotinamide | 408.9, 2.180$^a$ | 0.07 |
| 3 | 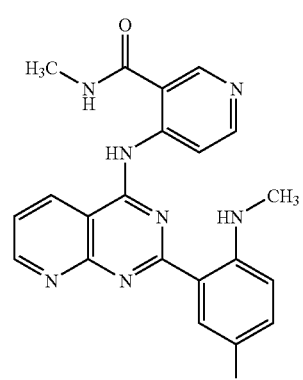 AutoNom Name: 4-[2-(5-Chloro-2-methylamino-phenyl)-pyrido[2,3-d]pyrimidin-4-ylamino]-N-methyl-nicotinamide | 419.9, 1.01 | 1.60 |
| 4 | 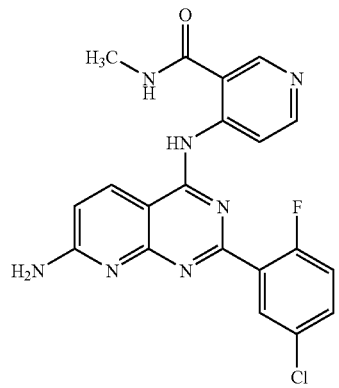 AutoNom Name: 4-[7-Amino-2-(5-chloro-2-fluoro-phenyl)-pyrido[2,3-d]pyrimidin-4-yl-amino]-N-methyl-nicotinamide | 422.1 | 0.03 |

TABLE 1-continued

| Compound No. | Structure | m/z (M + H+), retention time (min) | IC50 for Kinase Inhibition |
|---|---|---|---|
| 5 | 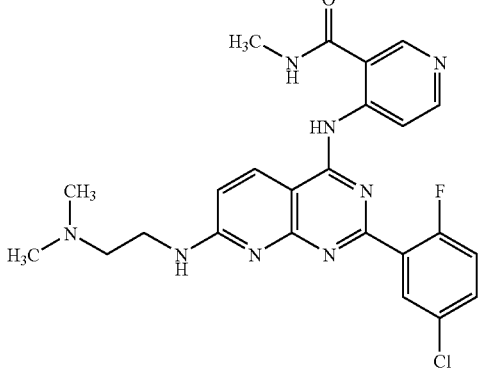 AutoNom Name: 4-[2-(5-Chloro-2-fluoro-phenyl)-7-(2-dimethylamino-ethylamino)-pyrido[2,3-d]pyrimidin-4-ylamino]-N-methyl-nicotinamide | 494, 0.87 | 6.04 |
| 6 | 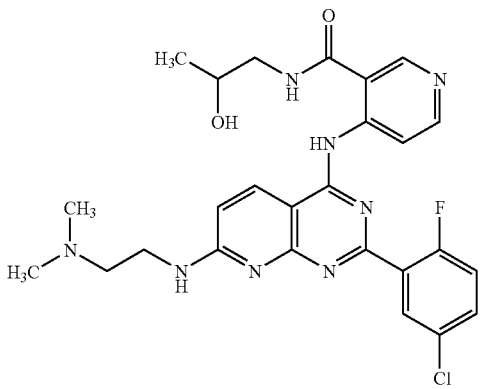 AutoNom Name: 4-[2-(5-Chloro-2-fluoro-phenyl)-7-(2-dimethylamino-ethylamino)-pyrido[2,3-d]pyrimidin-4-ylamino]-N-(2-hydroxy-propyl)-nicotinamide | 539, 0.81 | 12.20 |
| 7 | 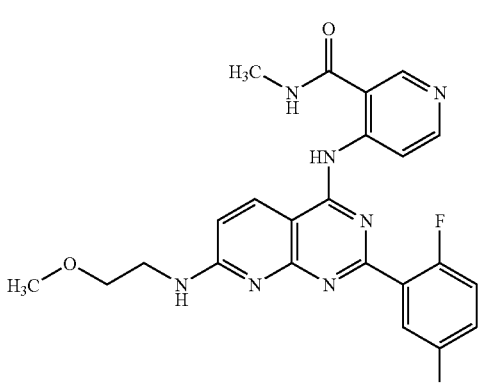 AutoNom Name: 4-[2-(5-Chloro-2-fluoro-phenyl)-7-(2-methoxy-ethylamino)-pyrido[2,3-d]pyrimidin-4-ylamino]-N-methyl-nicotinamide | 481, 1.07 | 0.98 |

TABLE 1-continued
| Compound No. | Structure | m/z (M + H+), retention time (min) | IC$_{50}$ for Kinase Inhibition |
|---|---|---|---|
| 8 | 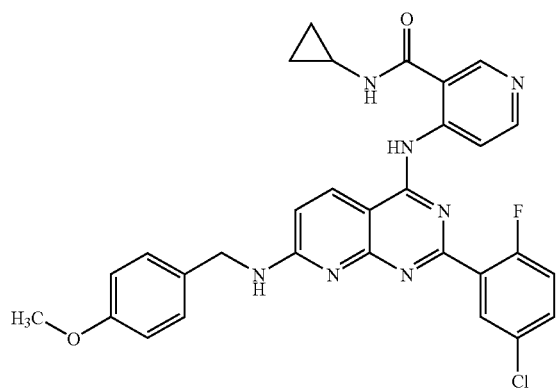 AutoNom Name: 4-[2-(5-Chloro-2-fluoro-phenyl)-7-(4-methoxy-benzylamino)-pyrido-[2,3-d]pyrimidin-4-ylamino]-N-cyclo-propyl-nicotinamide | 571, 1.41 | 1.40 |
| 9 | 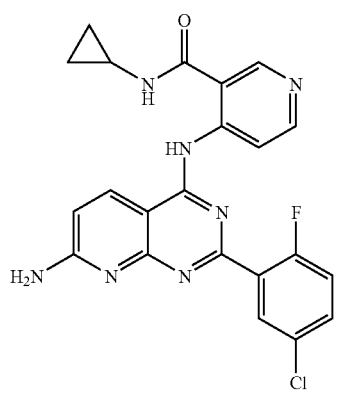 AutoNom Name: 4-[7-Amino-2-(5-chloro-2-fluoro-phenyl)-pyrido[2,3-d]pyrimidin-4-yl-amino]-N-cyclopropyl-nicotinamide | 449, 1.04 | 2.70 |

TABLE 1-continued

| Compound No. | Structure | m/z (M + H+), retention time (min) | IC$_{50}$ for Kinase Inhibition |
|---|---|---|---|
| 10 | 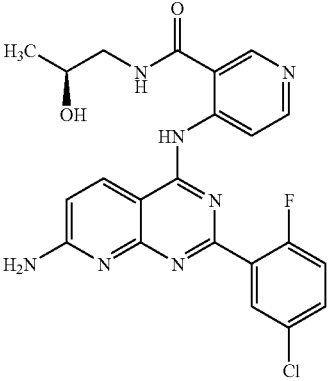<br>AutoNom Name:<br>4-[7-Amino-2-(5-chloro-2-fluoro-phenyl)-pyrido[2,3-d]pyrimidin-4-yl-amino]-N-(2-hydroxy-propyl)-nicotinamide | 467, 0.92 | 5.01 |

HPLC conditions used for the compounds in the Table:
HPLC solvents: A: water with 0.1% trifluoroacetic acid. B: acetonitrile with 0.1% trifluoroacetic acid.
HPLC Column: Merck AGA Chromolith Flash column (25 × 4.6 mm).
Standard Gradient: 5% B to 95% B over 2.5 minutes with a flow rate of 3.0 mL/Min.
$^a$Alternative Gradient: 5% B to 95% B over 4 minutes at a flow rate of 3.0 mL/Min.

Example 9

Activity of the Invention Compounds in HCV Replicon Assays

The pyrido[2,3-d]pyrimidine compounds of the present invention were examined for activity in the inhibition of HCV RNA replication in a cellular assay. The assay demonstrated that the tested compounds exhibit activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbored an RNA encoding a bicistronic expression construct comprising the wild type NS3-NS5B regions of HCV type Ib translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct was bordered by 5' and 3' NTRs (non-translated regions) from HCV type Ib. Continued culture of the replicon cells in the presence of G418 (neo$^R$) was dependent on the replication of the HCV RNA. The stably transfected replicon cells that expressed HCV RNA, which replicated autonomously and to high levels, encoding inter alia luciferase, were used for screening the antiviral compounds.

The replicon cells were plated in 384-well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures had high luciferase expression in the absence of any inhibitor. The inhibitory activity of the compound on luciferase activity was monitored on the Huh-Luc cells, enabling a dose-response curve for each test compound. EC$_{50}$ values were then calculated, which value represents the amount of the compound required to decrease by 50% the level of detected luciferase activity, or more specifically, the ability of the genetically linked HCV replicon RNA to replicate.

In Table 2, the HCV Replicon activity is provided for the tested compounds.

TABLE 2

| Compound Number | HCV Replicon activity (EC$_{50}$ in μM) |
|---|---|
| 1 | 0.76 |
| 2 | 11.9 |

The invention claimed is:
1. A compound, or pharmaceutically acceptable salt thereof, selected from the group consisting of:
   4-[2-(5-Chloro-2-fluoro-phenyl)-pyrido[2,3-d]pyrimidin-4-ylamino]-nicotinamide;
   4-[2-(5-Chloro-2-fluoro-phenyl)-pyrido[2,3-d]pyrimidin-4-ylamino]-N-methyl-nicotinamide;
   4-[2-(5-Chloro-2-methylamino-phenyl)-pyrido[2,3-d]pyrimidin-4-ylamino]-N-methyl-nicotinamide;
   4-[7-Amino-2-(5-Chloro-2-fluoro-phenyl)-pyrido[2,3-d]pyrimidin-4-ylamino]-N-methyl-nicotinamide;
   4-[2-(5-Chloro-2-fluoro-phenyl)-7-(2-dimethylamino-ethylamino)-pyrido[2,3-d]pyrimidin-4-ylamino]-N-methyl-nicotinamide;

4-[2-(5-Chloro-2-fluoro-phenyl)-7-(2-dimethylamino-ethylamino)-pyrido[2,3-d]pyrimidin-4-ylamino]-N-(2-hydroxy-propyl)-nicotinamide;

4-[2-(5-Chloro-2-fluoro-phenyl)-7-(2-methoxy-ethylamino)-pyrido[2,3-d]pyrimidin-4-ylamino]-N-methyl-nicotinamide;

4-[2-(5-Chloro-2-fluoro-phenyl)-7-(4-methoxy-benzylamino)-pyrido[2,3-d]pyrimidin-4-ylamino]-N-cyclopropyl-nicotinamide;

4-[7-Amino-2-(5-Chloro-2-fluoro-phenyl)-pyrido[2,3-d]pyrimidin-4-ylamino]-N-cyclopropyl-nicotinamide; and 4-[7-Amino-2-(5-Chloro-2-fluoro-phenyl)-pyrido[2,3-d]pyrimidin-4-ylamino]-N-(2-hydroxy-propyl)-nicotinamide.

2. A method of treating conditions associated with hepatitis C virus in a warm-blooded animal, comprising administering an effective amount of a compound, or pharmaceutically acceptable salts thereof, selected from the group consisting of:

4-[2-(5-Chloro-2-fluoro-phenyl)-pyrido[2,3-d]pyrimidin-4-ylamino]-nicotinamide;

4-[2-(5-Chloro-2-fluoro-phenyl)-pyrido[2,3-d]pyrimidin-4-ylamino]-N-methyl-nicotinamide;

4-[2-(5-Chloro-2-methylamino-phenyl)-pyrido[2,3-d]pyrimidin-4-ylamino]-N-methyl-nicotinamide;

4-[7-Amino-2-(5-Chloro-2-fluoro-phenyl)-pyrido[2,3-d]pyrimidin-4-ylamino]-N-methyl-nicotinamide;

4-[2-(5-Chloro-2-fluoro-phenyl)-7-(2-dimethylamino-ethylamino)-pyrido[2,3-d]pyrimidin-4-ylamino]-N-methyl-nicotinamide;

4-[2-(5-Chloro-2-fluoro-phenyl)-7-(2-dimethylamino-ethylamino)-pyrido[2,3-d]pyrimidin-4-ylamino]-N-(2-hydroxy-propyl)-nicotinamide;

4-[2-(5-Chloro-2-fluoro-phenyl)-7-(2-methoxy-ethylamino)-pyrido[2,3-d]pyrimidin-4-ylamino]-N-methyl-nicotinamide;

4-[2-(5-Chloro-2-fluoro-phenyl)-7-(4-methoxy-benzylamino)-pyrido[2,3-d]pyrimidin-4-ylamino]-N-cyclopropyl-nicotinamide;

4-[7-Amino-2-(5-Chloro-2-fluoro-phenyl)-pyrido[2,3-d]pyrimidin-4-ylamino]-N-cyclopropyl-nicotinamide; and 4-[7-Amino-2-(5-Chloro-2-fluoro-phenyl)-pyrido[2,3-d]pyrimidin-4-ylamino]-N-(2-hydroxy-propyl)-nicotinamide, and wherein said conditions are characterized by high levels of transforming growth factor-beta (TGFβ) activity and wherein said effective amount treats said conditions.

3. The method of claim 1, wherein the compound is 4-[2-(5-Chloro-2-fluoro-phenyl)-pyrido[2,3-d]pyrimidin-4-ylamino]-nicotinamide or a pharmaceutically acceptable salt thereof.

* * * * *